(12) United States Patent
McCabe

(10) Patent No.: US 9,944,487 B2
(45) Date of Patent: Apr. 17, 2018

(54) SINGLE TRANSFER INSERT PLACEMENT METHOD AND APPARATUS

(71) Applicant: John A. McCabe, Sheboygan Falls, WI (US)

(72) Inventor: John A. McCabe, Sheboygan Falls, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 643 days.

(21) Appl. No.: 13/875,090

(22) Filed: May 1, 2013

(65) Prior Publication Data

US 2013/0239764 A1    Sep. 19, 2013

Related U.S. Application Data

(60) Continuation-in-part of application No. 13/178,104, filed on Jul. 7, 2011, now Pat. No. 8,794,115, which
(Continued)

(51) Int. Cl.
*B65H 35/00*    (2006.01)
*B26D 7/01*    (2006.01)
(Continued)

(52) U.S. Cl.
CPC ... *B65H 35/0073* (2013.01); *A61F 13/15723* (2013.01); *A61F 13/15764* (2013.01);
(Continued)

(58) Field of Classification Search
CPC .... B65H 35/0073; B65H 35/08; B65H 39/14; B65H 2406/3452; B65H 2406/3612;
(Continued)

(56) References Cited

U.S. PATENT DOCUMENTS

| 135,145 A | 1/1873 | Murphy |
| 293,353 A | 2/1884 | Purvis |

(Continued)

FOREIGN PATENT DOCUMENTS

| BE | 1007854 | 11/1995 |
| CA | 1146129 | 5/1983 |

(Continued)

OTHER PUBLICATIONS

International Search Report dated Jan. 24, 2013 regarding EP Application No. 12167184.6, 5 pages.

(Continued)

*Primary Examiner* — Omar Flores Sanchez
(74) *Attorney, Agent, or Firm* — Ryan Kromholz & Manion, S.C.

(57) ABSTRACT

A web cutting system is provided for use with a single transfer insert placement mechanism having at least one puck for transferring a discrete web and a continuous web feeding mechanism for feeding a continuous web wherein first and second rollers having substantially parallel axes and being aligned with one another form a nip at their juncture, an anvil is attached to one roller, a die is attached to the other roller, a vacuum source is coupled to one of the rollers, a plurality of vacuum apertures is formed in the same roller. One of the rollers is positioned adjacent to the single transfer insert placement mechanism and to the continuous web feeding mechanism. The continuous web is applied to one roller and at least one discrete web is transferred from the puck to the same roller after which a die cutting process of the webs occurs at the nip.

10 Claims, 24 Drawing Sheets

Related U.S. Application Data is a division of application No. 12/070,879, filed on Feb. 21, 2008, now Pat. No. 7,975,584.

(60) Provisional application No. 61/642,237, filed on May 3, 2012, provisional application No. 60/902,477, filed on Feb. 21, 2007.

(51) Int. Cl.
*A61F 13/15* (2006.01)
*B26D 1/42* (2006.01)
*B65H 35/08* (2006.01)
*B65H 39/14* (2006.01)

(52) U.S. Cl.
CPC .......... *B26D 1/425* (2013.01); *B26D 7/018* (2013.01); *B65H 35/08* (2013.01); *B65H 39/14* (2013.01); *B65H 2301/33216* (2013.01); *B65H 2406/3452* (2013.01); *B65H 2406/3612* (2013.01); *B65H 2801/57* (2013.01); *Y10T 83/207* (2015.04)

(58) Field of Classification Search
CPC .......... B65H 2801/57; A61F 13/15723; A61F 13/15764; B26D 1/425; B26D 7/018; Y10T 83/207
USPC ............ 83/100; 198/377.01, 377.02, 377.03, 198/377.04
See application file for complete search history.

(56) References Cited

U.S. PATENT DOCUMENTS

| | | |
|---|---|---|
| 312,257 A | 2/1885 | Cotton et al. |
| 410,123 A | 8/1889 | Stilwell |
| 432,742 A | 7/1890 | Stanley |
| 643,821 A | 2/1900 | Howlett |
| 1,393,524 A | 10/1921 | Grupe |
| 1,431,315 A | 10/1922 | Le Moine |
| 1,605,842 A | 11/1926 | Jones |
| 1,686,595 A | 10/1928 | Belluche |
| 1,957,651 A | 5/1934 | Joa |
| 2,009,857 A | 7/1935 | Potdevin |
| 2,054,832 A | 9/1936 | Potdevin |
| 2,117,432 A | 5/1938 | Linscott |
| 2,128,746 A | 8/1938 | Joa |
| 2,131,808 A | 10/1938 | Joa |
| 2,164,408 A | 7/1939 | Joa |
| 2,167,179 A | 7/1939 | Joa |
| 2,171,741 A | 9/1939 | Cohn et al. |
| 2,213,431 A | 9/1940 | Joa |
| 2,254,290 A | 9/1941 | Joa |
| 2,254,291 A | 9/1941 | Joa |
| 2,282,477 A | 5/1942 | Joa |
| 2,286,096 A | 6/1942 | Joa |
| 2,296,931 A | 9/1942 | Joa |
| 2,304,571 A | 12/1942 | Joa |
| 2,324,930 A | 7/1943 | Joa |
| 2,345,937 A | 4/1944 | Joa |
| 2,466,240 A | 4/1949 | Joa |
| 2,481,929 A | 9/1949 | Joa |
| 2,510,229 A | 6/1950 | Joa |
| 2,540,844 A | 2/1951 | Strauss |
| 2,584,002 A | 1/1952 | Elser et al. |
| 2,591,359 A | 4/1952 | Joa |
| 2,618,816 A | 11/1952 | Joa |
| 2,627,859 A | 2/1953 | Hargrave |
| 2,659,437 A * | 11/1953 | Huck .................. B41F 13/60 493/356 |
| 2,695,025 A | 11/1954 | Andrews |
| 2,702,406 A | 2/1955 | Reed |
| 2,721,554 A | 10/1955 | Joa |
| 2,730,144 A | 1/1956 | Joa |
| 2,772,611 A | 12/1956 | Heywood |
| 2,780,253 A | 2/1957 | Joa |
| 2,785,609 A | 3/1957 | Billeb |
| 2,788,786 A | 4/1957 | Dexter |
| 2,811,905 A | 11/1957 | Kennedy, Jr. |
| 2,828,745 A | 4/1958 | Deutz |
| 2,839,059 A | 6/1958 | Joa |
| 2,842,169 A | 7/1958 | Joa |
| 2,851,934 A | 9/1958 | Heywood |
| 2,875,724 A | 3/1959 | Joa |
| 2,890,700 A | 6/1959 | Lonberg-Holm |
| 2,913,862 A | 11/1959 | Sabee |
| 2,939,461 A | 6/1960 | Joa |
| 2,939,646 A | 6/1960 | Stone |
| 2,960,143 A | 11/1960 | Joa |
| 2,990,081 A | 6/1961 | De Neui et al. |
| 2,991,739 A | 7/1961 | Joa |
| 3,016,207 A | 1/1962 | Comstock, III |
| 3,016,582 A | 1/1962 | Joa |
| 3,017,795 A | 1/1962 | Joa |
| 3,020,687 A | 2/1962 | Joa |
| 3,021,135 A | 2/1962 | Joa |
| 3,024,957 A | 3/1962 | Pinto |
| 3,053,427 A | 9/1962 | Wasserman |
| 3,054,516 A | 9/1962 | Joa |
| 3,069,982 A | 12/1962 | Heywood et al. |
| 3,075,684 A | 1/1963 | Rothmann |
| 3,086,253 A | 4/1963 | Joa |
| 3,087,689 A | 4/1963 | Heim |
| 3,089,494 A | 5/1963 | Schwartz |
| 3,091,408 A | 5/1963 | Schoeneman |
| 3,114,994 A | 12/1963 | Joa |
| 3,122,293 A | 2/1964 | Joa |
| 3,128,206 A | 4/1964 | Dungler |
| 3,203,419 A | 8/1965 | Joa |
| 3,230,955 A | 1/1966 | Joa |
| 3,268,954 A | 8/1966 | Joa |
| 3,288,037 A | 11/1966 | Burnett |
| 3,289,254 A | 12/1966 | Joa |
| 3,291,131 A | 12/1966 | Joa |
| 3,301,114 A | 1/1967 | Joa |
| 3,318,608 A | 5/1967 | Smrekar |
| 3,322,589 A | 5/1967 | Joa |
| 3,336,847 A | 8/1967 | Durat |
| 3,342,184 A | 9/1967 | Joa |
| 3,356,092 A | 12/1967 | Joa |
| 3,360,103 A | 12/1967 | Joa |
| 3,391,777 A | 7/1968 | Joa |
| 3,454,442 A | 7/1969 | Heller, Jr. |
| 3,463,413 A | 8/1969 | Smith |
| 3,470,848 A | 10/1969 | Dreher |
| 3,484,275 A | 12/1969 | Lewicki, Jr. |
| 3,502,322 A | 3/1970 | Cran |
| 3,521,639 A | 7/1970 | Joa |
| 3,526,563 A | 9/1970 | Schott, Jr. |
| 3,527,123 A | 9/1970 | Dovey |
| 3,538,551 A | 11/1970 | Joa |
| 3,540,641 A | 11/1970 | Besnyo |
| 3,575,170 A | 4/1971 | Clark |
| 3,607,578 A | 9/1971 | Berg et al. |
| 3,635,462 A | 1/1972 | Joa |
| 3,656,741 A | 4/1972 | Macke et al. |
| 3,666,611 A | 5/1972 | Joa |
| 3,673,021 A | 6/1972 | Joa |
| 3,685,818 A | 8/1972 | Burger et al. |
| 3,728,191 A | 4/1973 | Wierzba et al. |
| 3,751,224 A | 8/1973 | Wackerle |
| 3,758,102 A | 9/1973 | Munn et al. |
| 3,762,542 A | 10/1973 | Grimes |
| 3,772,120 A | 11/1973 | Radzins |
| 3,776,798 A | 12/1973 | Milano |
| 3,796,360 A | 3/1974 | Alexeff |
| 3,811,987 A | 5/1974 | Wilkinson et al. |
| 3,816,210 A | 6/1974 | Aoko et al. |
| 3,847,710 A | 11/1974 | Blomqvist et al. |
| 3,854,917 A | 12/1974 | McKinney et al. |
| 3,883,389 A | 5/1975 | Schott, Jr. |
| 3,888,400 A | 6/1975 | Wiig |
| 3,901,238 A | 8/1975 | Geller et al. |
| 3,903,768 A | 9/1975 | Amberg et al. |

(56) References Cited

U.S. PATENT DOCUMENTS

| | | |
|---|---|---|
| 3,904,147 A | 9/1975 | Taitel et al. |
| 3,918,968 A | 11/1975 | Coast |
| 3,921,481 A | 11/1975 | Fleetwod |
| 3,941,038 A | 3/1976 | Bishop |
| 3,960,646 A | 6/1976 | Wiedamann |
| 3,988,194 A | 10/1976 | Babcock et al. |
| 3,991,994 A | 11/1976 | Farish |
| 4,002,005 A | 1/1977 | Mueller et al. |
| 4,003,298 A | 1/1977 | Schott, Jr. |
| 4,009,626 A | 3/1977 | Gressman |
| 4,009,814 A | 3/1977 | Singh |
| 4,009,815 A | 3/1977 | Ericson et al. |
| 4,053,150 A | 10/1977 | Lane |
| 4,056,919 A | 11/1977 | Hirsch |
| 4,081,301 A | 3/1978 | Buell |
| 4,090,516 A | 5/1978 | Schaar |
| 4,094,319 A | 6/1978 | Joa |
| 4,103,595 A | 8/1978 | Corse |
| 4,106,974 A | 8/1978 | Hirsch |
| 4,108,584 A | 8/1978 | Radzins et al. |
| 4,136,535 A | 1/1979 | Audas |
| 4,141,193 A | 2/1979 | Joa |
| 4,141,509 A | 2/1979 | Radzins |
| 4,142,626 A | 3/1979 | Bradley |
| 4,157,934 A | 6/1979 | Ryan et al. |
| 4,165,666 A | 8/1979 | Johnson et al. |
| 4,168,776 A | 9/1979 | Hoeboer |
| 4,171,239 A | 10/1979 | Hirsch et al. |
| 4,205,679 A | 6/1980 | Repke et al. |
| 4,208,230 A | 6/1980 | Magarian |
| 4,213,356 A | 7/1980 | Armitage |
| 4,215,827 A | 8/1980 | Roberts et al. |
| 4,220,237 A | 9/1980 | Mohn |
| 4,222,533 A | 9/1980 | Pongracz |
| 4,223,822 A | 9/1980 | Clitheroe |
| 4,231,129 A | 11/1980 | Winch |
| 4,234,157 A | 11/1980 | Hodgeman et al. |
| 4,236,955 A | 12/1980 | Prittie |
| 4,275,510 A | 6/1981 | George |
| 4,284,454 A | 8/1981 | Joa |
| 4,307,800 A | 12/1981 | Joa |
| 4,316,756 A | 2/1982 | Wilson |
| 4,325,519 A | 4/1982 | McLean |
| 4,342,206 A | 8/1982 | Rommel |
| 4,349,140 A | 9/1982 | Passafiume |
| 4,364,787 A | 12/1982 | Radzins |
| 4,374,576 A | 2/1983 | Ryan |
| 4,379,008 A | 4/1983 | Gross et al. |
| 4,394,898 A | 7/1983 | Campbell |
| 4,411,721 A | 10/1983 | Wishart |
| 4,426,897 A | 1/1984 | Littleton |
| 4,452,597 A | 6/1984 | Achelpohl |
| 4,479,836 A | 10/1984 | Dickover et al. |
| 4,492,608 A | 1/1985 | Hirsch et al. |
| 4,501,098 A | 2/1985 | Gregory |
| 4,508,528 A | 4/1985 | Hirsch et al. |
| 4,522,853 A | 6/1985 | Szonn et al. |
| 4,543,152 A | 9/1985 | Nozaka |
| 4,551,191 A | 11/1985 | Kock et al. |
| 4,578,133 A | 3/1986 | Oshefsky et al. |
| 4,586,199 A | 5/1986 | Birring |
| 4,589,945 A | 5/1986 | Polit |
| 4,603,800 A | 8/1986 | Focke et al. |
| 4,606,964 A | 8/1986 | Wideman |
| 4,608,115 A | 8/1986 | Schroth et al. |
| 4,610,681 A | 9/1986 | Strohbeen et al. |
| 4,610,682 A | 9/1986 | Kopp |
| 4,614,076 A | 9/1986 | Rathemacher |
| 4,619,357 A | 10/1986 | Radzins et al. |
| 4,625,612 A | 12/1986 | Oliver |
| 4,634,482 A | 1/1987 | Lammers |
| 4,641,381 A | 2/1987 | Heran et al. |
| 4,642,150 A | 2/1987 | Stemmler |
| 4,642,839 A | 2/1987 | Urban |
| 4,650,530 A | 3/1987 | Mahoney et al. |
| 4,663,220 A | 5/1987 | Wisneski et al. |
| 4,672,705 A | 6/1987 | Bors et al. |
| 4,675,016 A | 6/1987 | Meuli et al. |
| 4,675,062 A | 6/1987 | Instance |
| 4,675,068 A | 6/1987 | Lundmark |
| 4,686,136 A | 8/1987 | Homonoff et al. |
| 4,693,056 A | 9/1987 | Raszewski |
| 4,701,239 A | 10/1987 | Craig |
| 4,720,415 A | 1/1988 | Vander Wielen et al. |
| 4,723,698 A | 2/1988 | Schoonderbeek |
| 4,726,874 A | 2/1988 | Van Vliet |
| 4,726,876 A | 2/1988 | Tomsovic, Jr. |
| 4,743,241 A | 5/1988 | Igaue et al. |
| 4,751,997 A | 6/1988 | Hirsch |
| 4,753,429 A | 6/1988 | Irvine et al. |
| 4,756,141 A | 7/1988 | Hirsch et al. |
| 4,757,732 A | 7/1988 | Arima |
| 4,764,325 A | 8/1988 | Angstadt |
| 4,765,780 A | 8/1988 | Angstadt |
| 4,776,920 A | 10/1988 | Ryan |
| 4,777,513 A | 10/1988 | Nelson |
| 4,782,647 A | 11/1988 | Williams et al. |
| 4,785,986 A | 11/1988 | Daane et al. |
| 4,795,451 A | 1/1989 | Buckley |
| 4,795,510 A | 1/1989 | Wittrock et al. |
| 4,798,353 A | 1/1989 | Peugh |
| 4,801,345 A | 1/1989 | Dussaud et al. |
| 4,802,570 A | 2/1989 | Hirsch et al. |
| 4,826,499 A | 5/1989 | Ahr |
| 4,840,609 A | 6/1989 | Jones et al. |
| 4,845,964 A | 7/1989 | Bors et al. |
| 4,864,802 A | 9/1989 | D'Angelo |
| 4,880,102 A | 11/1989 | Indrebo |
| 4,888,231 A | 12/1989 | Angstadt |
| 4,892,536 A | 1/1990 | Des Marais et al. |
| 4,904,440 A | 2/1990 | Angstadt |
| 4,908,175 A | 3/1990 | Angstadt |
| 4,909,019 A | 3/1990 | Delacretaz et al. |
| 4,915,767 A | 4/1990 | Rajala et al. |
| 4,917,746 A | 4/1990 | Kons |
| 4,925,520 A | 5/1990 | Beaudoin et al. |
| 4,927,322 A | 5/1990 | Schweizer et al. |
| 4,927,486 A | 5/1990 | Fattal et al. |
| 4,927,582 A | 5/1990 | Bryson |
| 4,937,887 A | 7/1990 | Schreiner |
| 4,963,072 A | 10/1990 | Miley et al. |
| 4,987,940 A | 1/1991 | Straub et al. |
| 4,994,010 A | 2/1991 | Doderer-Winkler |
| 5,000,806 A | 3/1991 | Merkatoris et al. |
| 5,021,111 A | 6/1991 | Swenson |
| 5,025,910 A | 6/1991 | Lasure et al. |
| 5,029,505 A | 7/1991 | Holliday |
| 5,045,039 A | 9/1991 | Bay |
| 5,045,135 A | 9/1991 | Meissner et al. |
| 5,062,597 A | 11/1991 | Martin et al. |
| 5,064,179 A | 11/1991 | Martin |
| 5,064,492 A | 11/1991 | Friesch |
| 5,080,741 A | 1/1992 | Nomura et al. |
| 5,094,658 A | 3/1992 | Smithe et al. |
| 5,096,532 A | 3/1992 | Neuwirth et al. |
| 5,108,017 A | 4/1992 | Adamski, Jr. et al. |
| 5,109,767 A | 5/1992 | Nyfeler et al. |
| 5,110,403 A | 5/1992 | Ehlert |
| 5,127,981 A | 7/1992 | Straub et al. |
| 5,131,525 A | 7/1992 | Musschoot |
| 5,131,901 A | 7/1992 | Moll |
| 5,133,511 A | 7/1992 | Mack |
| 5,147,487 A | 9/1992 | Nomura et al. |
| 5,163,594 A | 11/1992 | Meyer |
| 5,171,239 A | 12/1992 | Igaue et al. |
| 5,176,244 A | 1/1993 | Radzins et al. |
| 5,183,252 A | 2/1993 | Wolber et al. |
| 5,188,627 A | 2/1993 | Igaue et al. |
| 5,190,234 A | 3/1993 | Ezekiel |
| 5,195,684 A | 3/1993 | Radzins |
| 5,203,043 A | 4/1993 | Riedel |
| 5,213,645 A | 5/1993 | Nomura et al. |
| 5,222,422 A | 6/1993 | Benner, Jr. et al. |
| 5,223,069 A | 6/1993 | Tokuno et al. |

(56) References Cited

U.S. PATENT DOCUMENTS

| | | |
|---|---|---|
| 5,226,992 A | 7/1993 | Morman |
| 5,246,433 A | 9/1993 | Hasse et al. |
| 5,252,228 A | 10/1993 | Stokes |
| 5,267,933 A | 12/1993 | Precoma |
| 5,273,228 A | 12/1993 | Yoshida |
| 5,275,076 A | 1/1994 | Greenwalt |
| 5,275,676 A | 1/1994 | Rooyakkers et al. |
| 5,308,345 A | 5/1994 | Herrin |
| 5,328,438 A | 7/1994 | Crowley |
| 5,334,446 A | 8/1994 | Quantrille et al. |
| 5,340,424 A | 8/1994 | Matsushita |
| 5,353,909 A | 10/1994 | Mukai |
| 5,368,893 A | 11/1994 | Sommer et al. |
| 5,389,173 A | 2/1995 | Merkotoris et al. |
| 5,393,360 A | 2/1995 | Bridges et al. |
| 5,407,507 A | 4/1995 | Ball |
| 5,407,513 A * | 4/1995 | Hayden ............. A61F 13/15756 156/265 |
| 5,410,857 A | 5/1995 | Utley |
| 5,415,649 A | 5/1995 | Watanabe et al. |
| 5,417,132 A | 5/1995 | Cox et al. |
| 5,421,924 A | 6/1995 | Ziegelhoffer et al. |
| 5,424,025 A | 6/1995 | Hanschen et al. |
| 5,429,576 A | 7/1995 | Doderer-Winkler |
| 5,435,802 A | 7/1995 | Kober |
| 5,435,971 A | 7/1995 | Dyckman |
| 5,449,353 A | 9/1995 | Watanabe et al. |
| 5,464,401 A | 11/1995 | Hasse et al. |
| 5,486,253 A | 1/1996 | Otruba |
| 5,494,622 A | 2/1996 | Heath et al. |
| 5,500,075 A | 3/1996 | Herrmann |
| 5,516,392 A | 5/1996 | Bridges et al. |
| 5,518,566 A | 5/1996 | Bridges et al. |
| 5,525,175 A | 6/1996 | Blenke et al. |
| 5,531,850 A | 7/1996 | Herrmann |
| 5,540,647 A | 7/1996 | Weiermann et al. |
| 5,540,796 A | 7/1996 | Fries |
| 5,545,275 A | 8/1996 | Herrin et al. |
| 5,545,285 A | 8/1996 | Johnson |
| 5,552,013 A | 9/1996 | Ehlert et al. |
| 5,555,786 A | 9/1996 | Fuller |
| 5,556,360 A | 9/1996 | Kober et al. |
| 5,556,504 A | 9/1996 | Rajala et al. |
| 5,560,793 A | 10/1996 | Ruscher et al. |
| 5,575,187 A | 11/1996 | Dieterlen |
| 5,586,964 A | 12/1996 | Chase |
| 5,602,747 A | 2/1997 | Rajala |
| 5,603,794 A | 2/1997 | Thomas |
| 5,624,420 A | 4/1997 | Bridges et al. |
| 5,624,428 A | 4/1997 | Sauer |
| 5,628,738 A | 5/1997 | Suekane |
| 5,634,917 A | 6/1997 | Fujioka et al. |
| 5,636,500 A | 6/1997 | Gould |
| 5,643,165 A | 7/1997 | Klekamp |
| 5,643,396 A | 7/1997 | Rajala et al. |
| 5,645,543 A | 7/1997 | Nomura et al. |
| 5,659,229 A | 8/1997 | Rajala |
| 5,660,657 A | 8/1997 | Rajala et al. |
| 5,660,665 A | 8/1997 | Jalonen |
| 5,683,376 A | 11/1997 | Kato et al. |
| 5,683,531 A | 11/1997 | Roessler et al. |
| 5,685,873 A | 11/1997 | Bruemmer |
| RE35,687 E | 12/1997 | Igaue et al. |
| 5,693,165 A | 12/1997 | Schmitz |
| 5,699,653 A | 12/1997 | Hartman et al. |
| 5,705,013 A | 1/1998 | Nease |
| 5,707,470 A | 1/1998 | Rajala et al. |
| 5,711,832 A | 1/1998 | Glaug et al. |
| 5,725,518 A | 3/1998 | Coates |
| 5,725,714 A | 3/1998 | Fujioka |
| 5,743,994 A | 4/1998 | Roessler et al. |
| 5,745,922 A | 5/1998 | Rajala et al. |
| 5,746,869 A | 5/1998 | Hayden et al. |
| 5,749,989 A | 5/1998 | Linman et al. |
| 5,759,340 A | 6/1998 | Boothe et al. |
| 5,766,389 A | 6/1998 | Brandon et al. |
| 5,766,411 A | 6/1998 | Wilson |
| 5,779,689 A | 7/1998 | Pfeifer et al. |
| 5,788,797 A | 8/1998 | Herrin et al. |
| 5,817,199 A | 10/1998 | Brennecke et al. |
| 5,827,259 A | 10/1998 | Laux et al. |
| 5,829,164 A | 11/1998 | Kotischke |
| 5,836,931 A | 11/1998 | Toyoda et al. |
| 5,858,012 A | 1/1999 | Yamaki et al. |
| 5,865,393 A | 2/1999 | Kreft et al. |
| 5,868,727 A | 2/1999 | Barr et al. |
| 5,876,027 A | 3/1999 | Fukui et al. |
| 5,876,792 A | 3/1999 | Caldwell |
| 5,879,500 A | 3/1999 | Herrin et al. |
| 5,902,431 A | 5/1999 | Wilkinson et al. |
| 5,904,675 A | 5/1999 | Laux et al. |
| 5,932,039 A | 8/1999 | Popp et al. |
| 5,935,367 A | 8/1999 | Hollenbeck |
| 5,938,193 A | 8/1999 | Bluemle et al. |
| 5,938,652 A | 8/1999 | Sauer |
| 5,964,390 A | 10/1999 | Borresen et al. |
| 5,964,970 A | 10/1999 | Woolwine et al. |
| 5,971,134 A | 10/1999 | Trefz et al. |
| 5,983,764 A | 11/1999 | Hillebrand |
| 6,009,781 A | 1/2000 | McNeil |
| 6,022,443 A | 2/2000 | Rajala et al. |
| 6,036,805 A | 3/2000 | McNichols |
| 6,043,836 A | 3/2000 | Kerr et al. |
| 6,050,517 A | 4/2000 | Dobrescu et al. |
| 6,074,110 A | 6/2000 | Verlinden et al. |
| 6,076,442 A | 6/2000 | Arterburn et al. |
| 6,080,909 A | 6/2000 | Osterdahl et al. |
| 6,098,249 A | 8/2000 | Toney et al. |
| 6,123,792 A | 9/2000 | Samida et al. |
| 6,142,048 A | 11/2000 | Bradatsch et al. |
| 6,171,432 B1 | 1/2001 | Brisebois |
| 6,183,576 B1 | 2/2001 | Couillard et al. |
| 6,193,054 B1 | 2/2001 | Henson et al. |
| 6,193,702 B1 | 2/2001 | Spencer |
| 6,195,850 B1 | 3/2001 | Melbye |
| 6,210,386 B1 | 4/2001 | Inoue |
| 6,212,859 B1 | 4/2001 | Bielik, Jr. et al. |
| 6,214,147 B1 | 4/2001 | Mortellite et al. |
| 6,250,048 B1 | 6/2001 | Linkiewicz |
| 6,264,639 B1 | 7/2001 | Sauer |
| 6,264,784 B1 | 7/2001 | Menard et al. |
| 6,276,421 B1 | 8/2001 | Valenti et al. |
| 6,276,587 B1 | 8/2001 | Borresen |
| 6,280,373 B1 | 8/2001 | Lanvin |
| 6,284,081 B1 | 9/2001 | Vogt et al. |
| 6,287,409 B1 | 9/2001 | Stephany |
| 6,305,260 B1 | 10/2001 | Truttmann et al. |
| 6,306,122 B1 | 10/2001 | Narawa et al. |
| 6,309,336 B1 | 10/2001 | Muessig et al. |
| 6,312,420 B1 | 11/2001 | Sasaki et al. |
| 6,314,333 B1 | 11/2001 | Rajala et al. |
| 6,315,022 B1 | 11/2001 | Herrin et al. |
| 6,319,347 B1 | 11/2001 | Rajala |
| 6,336,921 B1 | 1/2002 | Kato et al. |
| 6,336,922 B1 | 1/2002 | VanGompel et al. |
| 6,336,923 B1 | 1/2002 | Fujioka et al. |
| 6,358,350 B1 | 3/2002 | Glaug et al. |
| 6,369,291 B1 | 4/2002 | Uchimoto et al. |
| 6,375,769 B1 | 4/2002 | Quereshi et al. |
| 6,391,013 B1 | 5/2002 | Suzuki et al. |
| 6,416,697 B1 | 7/2002 | Venturino et al. |
| 6,431,038 B2 | 8/2002 | Couturier |
| 6,440,246 B1 | 8/2002 | Vogt et al. |
| 6,443,389 B1 | 9/2002 | Palone |
| 6,446,795 B1 | 9/2002 | Allen et al. |
| 6,473,669 B2 | 10/2002 | Rajala et al. |
| 6,475,325 B1 | 11/2002 | Parrish et al. |
| 6,478,786 B1 | 11/2002 | Glaug et al. |
| 6,482,278 B1 | 11/2002 | McCabe et al. |
| 6,494,244 B2 | 12/2002 | Parrish et al. |
| 6,514,233 B1 | 2/2003 | Glaug |
| 6,521,320 B2 | 2/2003 | McCabe et al. |
| 6,523,595 B1 | 2/2003 | Milner et al. |
| 6,524,423 B1 | 2/2003 | Hilt et al. |

(56) References Cited

U.S. PATENT DOCUMENTS

| | | |
|---|---|---|
| 6,533,879 B2 | 3/2003 | Quereshi et al. |
| 6,540,857 B1 | 4/2003 | Coenen et al. |
| 6,547,909 B1 | 4/2003 | Butterworth |
| 6,550,517 B1 | 4/2003 | Hilt et al. |
| 6,551,228 B1 | 4/2003 | Richards |
| 6,551,430 B1 | 4/2003 | Glaug et al. |
| 6,554,815 B1 | 4/2003 | Umebayashi |
| 6,569,275 B1 | 5/2003 | Popp et al. |
| 6,572,520 B2 | 6/2003 | Blumle |
| 6,581,517 B1 | 6/2003 | Becker et al. |
| 6,585,841 B1 | 7/2003 | Popp et al. |
| 6,589,149 B1 | 7/2003 | VanEperen et al. |
| 6,596,107 B2 | 7/2003 | Stopher |
| 6,596,108 B2 | 7/2003 | McCabe |
| 6,605,172 B1 | 8/2003 | Anderson et al. |
| 6,605,173 B2 | 8/2003 | Glaug et al. |
| 6,620,276 B1 | 9/2003 | Kuntze et al. |
| 6,634,269 B2 | 10/2003 | Eckstein et al. |
| 6,637,583 B1 | 10/2003 | Anderson |
| 6,648,122 B1 | 11/2003 | Hirsch et al. |
| 6,649,010 B2 | 11/2003 | Parrish et al. |
| 6,656,309 B1 | 12/2003 | Parker et al. |
| 6,659,150 B1 | 12/2003 | Perkins et al. |
| 6,659,991 B2 | 12/2003 | Suckane |
| 6,675,552 B2 | 1/2004 | Kunz et al. |
| 6,682,626 B2 | 1/2004 | Mlinar et al. |
| 6,684,925 B2 | 2/2004 | Nagate et al. |
| 6,722,494 B2 | 4/2004 | Nakakado |
| 6,730,189 B1 | 5/2004 | Franzmann |
| 6,743,324 B2 | 6/2004 | Hargett et al. |
| 6,750,466 B2 | 6/2004 | Song |
| 6,758,109 B2 | 7/2004 | Nakakado |
| 6,766,817 B2 | 7/2004 | da Silva |
| 6,779,426 B1 | 8/2004 | Holliday |
| 6,808,582 B2 | 10/2004 | Popp et al. |
| D497,991 S | 11/2004 | Otsubo et al. |
| 6,811,019 B2 | 11/2004 | Christian et al. |
| 6,811,642 B2 | 11/2004 | Ochi |
| 6,814,217 B2 | 11/2004 | Blumenthal et al. |
| 6,820,671 B2 | 11/2004 | Calvert |
| 6,837,840 B2 | 1/2005 | Yonekawa et al. |
| 6,840,616 B2 | 1/2005 | Summers |
| 6,869,494 B2 | 3/2005 | Roessler et al. |
| 6,875,202 B2 | 4/2005 | Kumasaka et al. |
| 6,884,310 B2 | 4/2005 | Roessler et al. |
| 6,893,528 B2 | 5/2005 | Middelstadt et al. |
| 6,913,718 B2 | 7/2005 | Ducker |
| 6,918,404 B2 | 7/2005 | Dias da Silva |
| 6,852,186 B1 | 12/2005 | Matsuda et al. |
| 6,976,521 B2 | 12/2005 | Mlinar |
| 6,978,486 B2 | 12/2005 | Zhou et al. |
| 7,017,321 B2 | 3/2006 | Salvoni |
| 7,017,820 B1 | 3/2006 | Brunner |
| 7,045,031 B2 | 5/2006 | Popp et al. |
| 7,047,852 B2 | 5/2006 | Franklin et al. |
| 7,048,725 B2 | 5/2006 | Kling et al. |
| 7,066,586 B2 | 6/2006 | da Silva |
| 7,069,970 B2 | 7/2006 | Tomsovic et al. |
| 7,077,393 B2 | 7/2006 | Ishida |
| 7,130,710 B2 | 10/2006 | Shechtman |
| 7,137,971 B2 | 11/2006 | Tanzer |
| 7,172,666 B2 | 2/2007 | Groves et al. |
| 7,175,584 B2 | 2/2007 | Maxton et al. |
| 7,195,684 B2 | 3/2007 | Satoh |
| 7,201,345 B2 | 4/2007 | Werner |
| 7,214,174 B2 | 5/2007 | Allen et al. |
| 7,214,287 B2 | 5/2007 | Shiomi |
| 7,220,335 B2 | 5/2007 | Van Gompel et al. |
| 7,247,219 B2 | 7/2007 | O'Dowd |
| 7,252,730 B2 | 8/2007 | Hoffman et al. |
| 7,264,686 B2 | 9/2007 | Thorson et al. |
| 7,303,708 B2 | 12/2007 | Andrews et al. |
| 7,326,311 B2 | 2/2008 | Krueger et al. |
| 7,332,459 B2 | 2/2008 | Collins et al. |
| 7,374,627 B2 | 5/2008 | McCabe |
| 7,380,213 B2 | 5/2008 | Pesin |
| 7,398,870 B2 | 7/2008 | McCabe |
| 7,449,084 B2 | 11/2008 | Nakakado |
| 7,452,436 B2 | 11/2008 | Andrews |
| 7,533,709 B2 | 5/2009 | Meyer |
| 7,537,215 B2 | 5/2009 | Beaudoin et al. |
| 7,587,966 B2 | 9/2009 | Nakakado et al. |
| 7,618,513 B2 | 11/2009 | Meyer |
| 7,638,014 B2 | 12/2009 | Coose et al. |
| 7,640,962 B2 | 1/2010 | Meyer et al. |
| 7,695,464 B2 | 4/2010 | Fletcher et al. |
| 7,703,599 B2 | 4/2010 | Meyer |
| 7,708,849 B2 | 5/2010 | McCabe |
| 7,770,712 B2 | 8/2010 | McCabe |
| 7,771,407 B2 | 8/2010 | Umebayashi |
| 7,780,052 B2 * | 8/2010 | McCabe ........... A61F 13/15723 156/510 |
| 7,793,772 B2 | 9/2010 | Schafer |
| 7,811,403 B2 | 10/2010 | Andrews |
| 7,861,756 B2 | 1/2011 | Jenquin et al. |
| 7,871,400 B2 | 1/2011 | Sablone et al. |
| 7,909,956 B2 | 3/2011 | Coose et al. |
| 7,922,983 B2 | 4/2011 | Prokash et al. |
| 7,935,296 B2 | 5/2011 | Koele et al. |
| 7,975,584 B2 | 7/2011 | McCabe |
| 7,987,964 B2 | 8/2011 | McCabe |
| 8,007,484 B2 | 8/2011 | McCabe et al. |
| 8,007,623 B2 | 8/2011 | Andrews |
| 8,011,493 B2 | 9/2011 | Giuliani et al. |
| 8,016,972 B2 | 9/2011 | Andrews et al. |
| 8,025,652 B2 | 9/2011 | Hornung et al. |
| 8,062,459 B2 | 11/2011 | Nakakado et al. |
| 8,100,173 B2 | 1/2012 | Hornung et al. |
| 8,172,977 B2 | 5/2012 | Andrews et al. |
| 8,176,573 B2 | 5/2012 | Popp et al. |
| 8,178,035 B2 | 5/2012 | Edvardsson et al. |
| 8,182,624 B2 | 5/2012 | Handziak |
| 8,182,735 B2 | 5/2012 | Edvardsson |
| 8,182,736 B2 | 5/2012 | Edvardsson |
| 8,293,056 B2 | 10/2012 | McCabe |
| 8,381,489 B2 | 2/2013 | Freshwater et al. |
| 8,398,793 B2 | 3/2013 | Andrews et al. |
| 8,417,374 B2 | 4/2013 | Meyer et al. |
| 8,460,495 B2 | 6/2013 | McCabe |
| 8,512,496 B2 | 8/2013 | Makimura |
| 2001/0012813 A1 | 8/2001 | Bluemle |
| 2001/0017181 A1 | 8/2001 | Otruba et al. |
| 2001/0035332 A1 | 11/2001 | Zeitler |
| 2001/0042591 A1 | 11/2001 | Milner et al. |
| 2002/0040630 A1 | 4/2002 | Piazza |
| 2002/0046802 A1 | 4/2002 | Tachibana et al. |
| 2002/0059013 A1 | 5/2002 | Rajala et al. |
| 2002/0096241 A1 | 7/2002 | Instance |
| 2002/0125105 A1 | 9/2002 | Nakakado |
| 2002/0162776 A1 | 11/2002 | Hergeth |
| 2003/0000620 A1 | 1/2003 | Herrin et al. |
| 2003/0015209 A1 | 1/2003 | Gingras et al. |
| 2003/0115660 A1 | 1/2003 | Hopkins |
| 2003/0051802 A1 | 3/2003 | Hargett et al. |
| 2003/0052148 A1 | 3/2003 | Rajala et al. |
| 2003/0066585 A1 | 4/2003 | McCabe |
| 2003/0083638 A1 | 5/2003 | Molee |
| 2003/0084984 A1 | 5/2003 | Glaug et al. |
| 2003/0089447 A1 | 5/2003 | Molee et al. |
| 2003/0121244 A1 | 7/2003 | Abba |
| 2003/0121614 A1 | 7/2003 | Tabor et al. |
| 2003/0135189 A1 | 7/2003 | Umebayashi |
| 2003/0150551 A1 | 8/2003 | Baker |
| 2004/0007328 A1 | 1/2004 | Popp et al. |
| 2004/0016500 A1 | 1/2004 | Tachibana et al. |
| 2004/0044325 A1 | 3/2004 | Corneliusson |
| 2004/0073187 A1 | 4/2004 | Karami |
| 2004/0087425 A1 | 5/2004 | Ng et al. |
| 2004/0098791 A1 | 5/2004 | Faulks |
| 2004/0112517 A1 | 6/2004 | Groves et al. |
| 2004/0164482 A1 | 8/2004 | Edinger |
| 2004/0167493 A1 | 8/2004 | Jarpenberg et al. |
| 2004/0177737 A1 | 9/2004 | Adami |
| 2004/0182213 A1 | 9/2004 | Wagner et al. |

(56) References Cited

U.S. PATENT DOCUMENTS

| | | |
|---|---|---|
| 2004/0182497 A1 | 9/2004 | Lowrey |
| 2004/0216830 A1 | 11/2004 | Van Eperen |
| 2005/0000628 A1 | 1/2005 | Norrby |
| 2005/0022476 A1 | 2/2005 | Hamer |
| 2005/0056678 A1 | 3/2005 | Nomura et al. |
| 2005/0077418 A1 | 4/2005 | Werner et al. |
| 2005/0196538 A1 | 9/2005 | Sommer et al. |
| 2005/0230056 A1 | 10/2005 | Meyer et al. |
| 2005/0230449 A1 | 10/2005 | Meyer et al. |
| 2005/0233881 A1 | 10/2005 | Meyer |
| 2005/0234412 A1 | 10/2005 | Andrews et al. |
| 2005/0257881 A1 | 11/2005 | Coose et al. |
| 2005/0275148 A1 | 12/2005 | Beaudoin et al. |
| 2006/0011030 A1 | 1/2006 | Wagner et al. |
| 2006/0021300 A1 | 2/2006 | Tada et al. |
| 2006/0137298 A1 | 6/2006 | Oshita et al. |
| 2006/0201619 A1 | 9/2006 | Andrews |
| 2006/0224137 A1 | 10/2006 | McCabe et al. |
| 2006/0265867 A1 | 11/2006 | Schaap |
| 2007/0074953 A1 | 4/2007 | McCabe |
| 2007/0131343 A1 | 6/2007 | Nordang |
| 2007/0131817 A1 | 6/2007 | Fromm |
| 2008/0041206 A1 | 2/2008 | Mergola et al. |
| 2008/0210067 A1 | 9/2008 | Schlinz et al. |
| 2008/0223537 A1 | 9/2008 | Wiedmann |
| 2008/0281286 A1 | 11/2008 | Peterson |
| 2008/0287898 A1 | 11/2008 | Guzman |
| 2009/0020211 A1 | 1/2009 | Andrews et al. |
| 2009/0126864 A1 | 5/2009 | Tachibana et al. |
| 2009/0198205 A1 | 8/2009 | Malowaniec et al. |
| 2009/0212468 A1 | 8/2009 | Edvardsson et al. |
| 2009/0321021 A1* | 12/2009 | Yamamoto ........ A61F 13/15723 156/511 |
| 2010/0078119 A1 | 4/2010 | Yamamoto |
| 2010/0078120 A1 | 4/2010 | Otsubo |
| 2010/0078127 A1 | 4/2010 | Yamamoto |
| 2010/0193135 A1 | 8/2010 | Eckstein et al. |
| 2010/0193138 A1 | 8/2010 | Eckstein |
| 2010/0193155 A1 | 8/2010 | Nakatani |
| 2010/0249737 A1 | 9/2010 | Ito et al. |
| 2011/0106042 A1 | 5/2011 | Sablone et al. |
| 2012/0079926 A1 | 4/2012 | Long et al. |
| 2012/0123377 A1 | 5/2012 | Back |
| 2012/0270715 A1 | 10/2012 | Motegi et al. |
| 2012/0285306 A1 | 11/2012 | Weibelt |
| 2012/0310193 A1 | 12/2012 | Ostertag |
| 2012/0312463 A1 | 12/2012 | Ogasawara et al. |
| 2013/0035222 A1* | 2/2013 | Andrews ........... A61F 13/15723 493/342 |
| 2013/0037201 A1* | 2/2013 | Pagel ................ A61F 13/15723 156/73.1 |
| 2014/0001681 A1* | 1/2014 | Hargett ............ A61F 13/15593 264/571 |

FOREIGN PATENT DOCUMENTS

| | | |
|---|---|---|
| CA | 1153345 | 9/1983 |
| CA | 1190078 | 7/1985 |
| CA | 1210744 | 9/1986 |
| CA | 1212132 | 9/1986 |
| CA | 1236056 | 5/1988 |
| CA | 1249102 | 1/1989 |
| CA | 1292201 | 11/1991 |
| CA | 1307244 | 9/1992 |
| CA | 1308015 | 9/1992 |
| CA | 1310342 | 11/1992 |
| CA | 2023816 | 3/1994 |
| CA | 2330679 | 9/1999 |
| CA | 2404154 | 10/2001 |
| CA | 2541194 | 10/2006 |
| CA | 2559517 | 4/2007 |
| CA | 2337700 | 8/2008 |
| CA | 2407867 | 6/2010 |
| CA | 2699136 | 10/2010 |
| CA | 142627 | 6/2013 |
| CA | 2600432 | 7/2013 |
| CN | 202105105 | 1/2012 |
| DE | 60123502 | 10/2006 |
| DE | 60216550 | 12/2006 |
| DE | 102005035544 | 2/2007 |
| DE | 102005048868 | 4/2007 |
| DE | 102006047280 | 4/2007 |
| DE | 102007063209 | 6/2009 |
| EP | 0044206 | 1/1982 |
| EP | 0048011 | 3/1982 |
| EP | 0089106 | 9/1983 |
| EP | 0099732 | 2/1984 |
| EP | 0206208 | 12/1986 |
| EP | 0304140 | 2/1989 |
| EP | 0411287 | 2/1991 |
| EP | 0439897 | 8/1991 |
| EP | 0455231 A1 | 11/1991 |
| EP | 510251 | 10/1992 |
| EP | 0589859 | 3/1994 |
| EP | 0676352 | 4/1995 |
| EP | 0652175 A1 | 5/1995 |
| EP | 0811473 | 12/1997 |
| EP | 0901780 | 3/1999 |
| EP | 0990588 | 4/2000 |
| EP | 1132325 A2 | 9/2001 |
| EP | 1035818 | 4/2002 |
| EP | 1199057 | 4/2002 |
| EP | 1366734 | 12/2003 |
| EP | 1393701 | 3/2004 |
| EP | 1415628 | 5/2004 |
| EP | 1433731 | 6/2004 |
| EP | 1571249 | 9/2005 |
| EP | 1619008 | 1/2006 |
| EP | 1707168 A2 | 10/2006 |
| EP | 1726414 | 11/2006 |
| EP | 1302424 | 12/2006 |
| EP | 1801045 | 6/2007 |
| EP | 1941853 | 7/2008 |
| EP | 1961403 | 8/2008 |
| EP | 1994919 | 11/2008 |
| EP | 2180864 | 11/2008 |
| EP | 2211812 | 11/2008 |
| EP | 2103427 | 9/2009 |
| EP | 2233116 | 9/2010 |
| EP | 2238955 | 10/2010 |
| EP | 1175880 | 5/2012 |
| EP | 1868821 | 1/2013 |
| EP | 2036522 | 3/2013 |
| EP | 1272347 | 4/2013 |
| EP | 2032338 | 8/2013 |
| ES | 509706 | 11/1982 |
| ES | 520559 | 12/1983 |
| ES | 296211 | 12/1987 |
| ES | 200601373 | 7/2009 |
| ES | 2311349 | 9/2009 |
| FR | 2177355 | 11/1973 |
| FR | 2255961 | 7/1975 |
| FR | 1132325 | 10/2006 |
| FR | 2891811 | 4/2007 |
| GB | 191101501 A | 1/1912 |
| GB | 439897 | 12/1935 |
| GB | 856389 | 12/1960 |
| GB | 941073 | 11/1963 |
| GB | 1096373 | 12/1967 |
| GB | 1126539 | 9/1968 |
| GB | 1346329 | 2/1974 |
| GB | 1412812 | 11/1975 |
| GB | 1467470 | 3/1977 |
| GB | 2045298 | 10/1980 |
| GB | 2115775 | 9/1983 |
| GB | 2288316 | 10/1995 |
| IT | 1374910 | 5/2010 |
| IT | 1374911 | 5/2010 |
| JP | 428364 | 1/1992 |
| JP | 542180 | 2/1993 |
| JP | 576566 | 3/1993 |
| JP | 626160 | 2/1994 |
| JP | 626161 | 2/1994 |

(56) References Cited

FOREIGN PATENT DOCUMENTS

| | | |
|---|---|---|
| JP | 6197925 A | 7/1994 |
| JP | 9299398 | 11/1997 |
| JP | 10035621 | 2/1998 |
| JP | 10-277091 A | 10/1998 |
| JP | 2008-161300 | 7/2008 |
| SE | 0602047 | 5/2007 |
| SE | 0601003-7 | 6/2007 |
| SE | 0601145-6 | 10/2009 |
| WO | WO08155618 | 12/1988 |
| WO | WO93/15248 | 8/1993 |
| WO | WO9403301 | 2/1994 |
| WO | WO97/23398 | 7/1997 |
| WO | WO9732552 | 9/1997 |
| WO | WO9747265 | 12/1997 |
| WO | WO9747810 | 12/1997 |
| WO | WO9821134 | 5/1998 |
| WO | WO98/55298 | 12/1998 |
| WO | WO9907319 | 2/1999 |
| WO | WO9913813 A1 | 3/1999 |
| WO | WO9932385 | 7/1999 |
| WO | WO9965437 | 12/1999 |
| WO | WO0143682 | 6/2001 |
| WO | WO0172237 A2 | 10/2001 |
| WO | WO2003/031177 | 4/2003 |
| WO | WO04007329 | 1/2004 |
| WO | WO05075163 | 8/2005 |
| WO | WO2006038946 | 4/2006 |
| WO | WO07029115 | 3/2007 |
| WO | WO07039800 | 4/2007 |
| WO | WO2007126347 | 11/2007 |
| WO | WO08001209 | 1/2008 |
| WO | WO2008/015594 | 2/2008 |
| WO | WO2008037281 | 4/2008 |
| WO | WO2008/123348 | 10/2008 |
| WO | WO2009/065497 | 3/2009 |
| WO | WO2009/065500 | 3/2009 |
| WO | WO2010028786 | 3/2010 |
| WO | WO2011101773 | 8/2011 |

OTHER PUBLICATIONS

International Search Report dated Jan. 24, 2013 regarding EP Application No. 12167183.8, 8 pages.
International Search Report dated Aug. 8, 2013 regarding EP Application No. 13166330.4, 7 pages.
International Search Report dated Aug. 16, 2013 regarding EP Application No. 13166314.8, 6 pages.

* cited by examiner

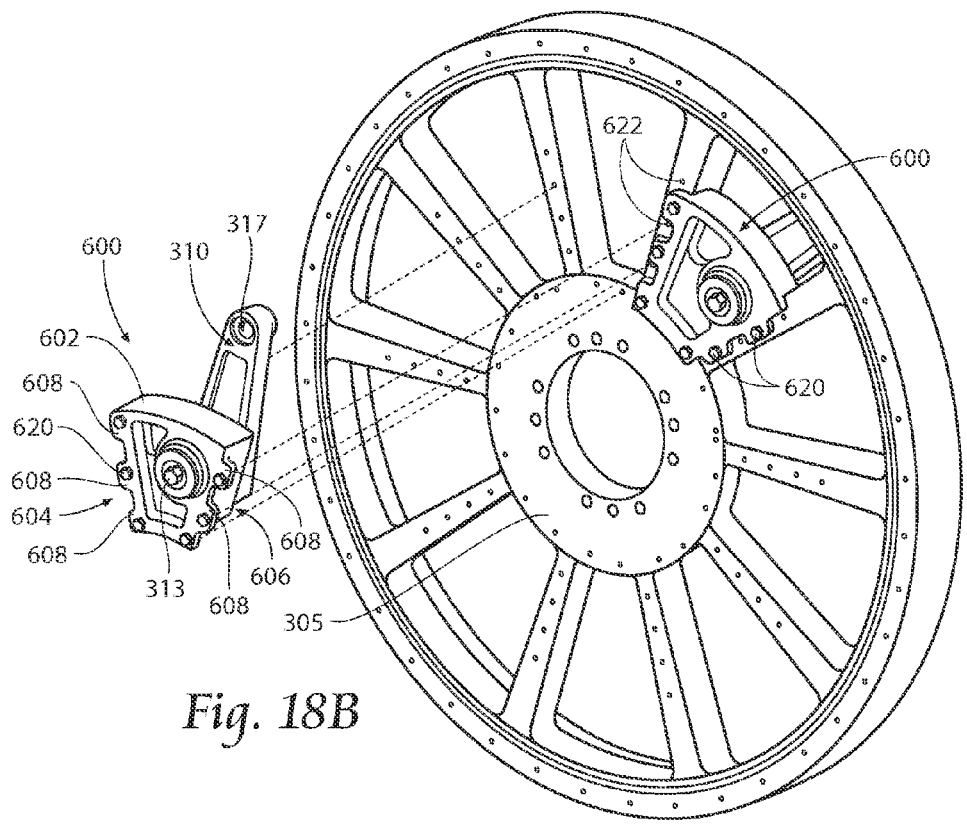
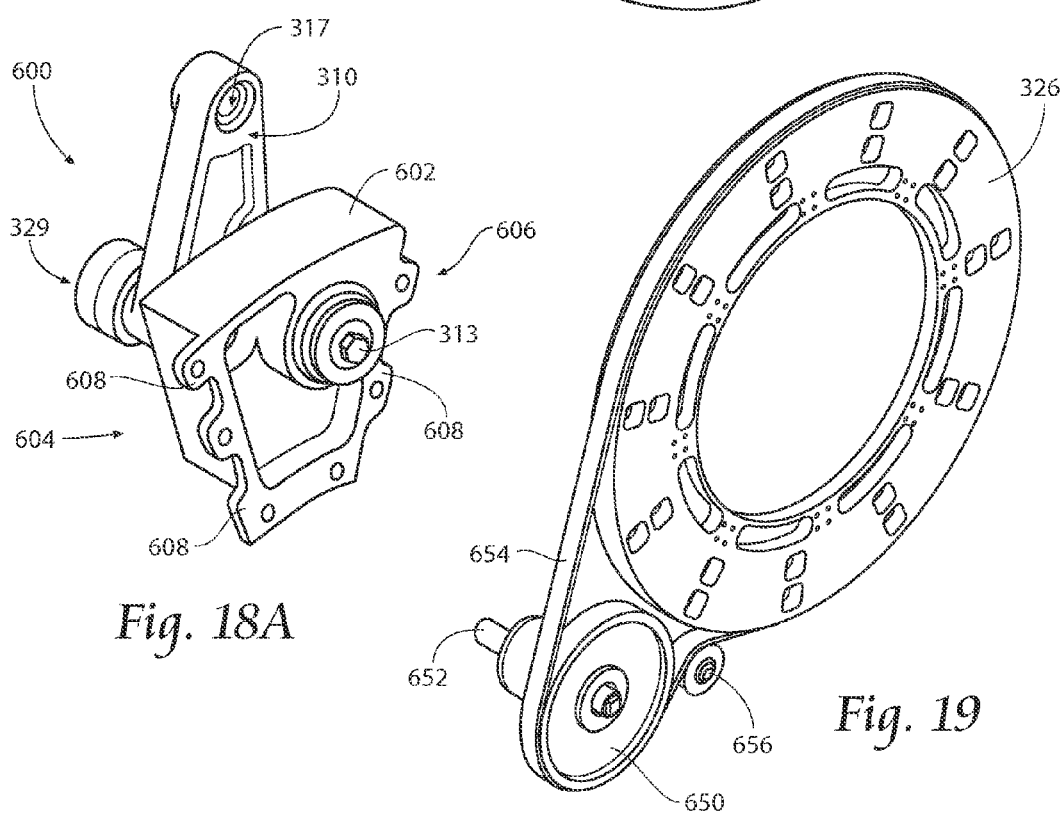
Fig. 18B
Fig. 18A
Fig. 19

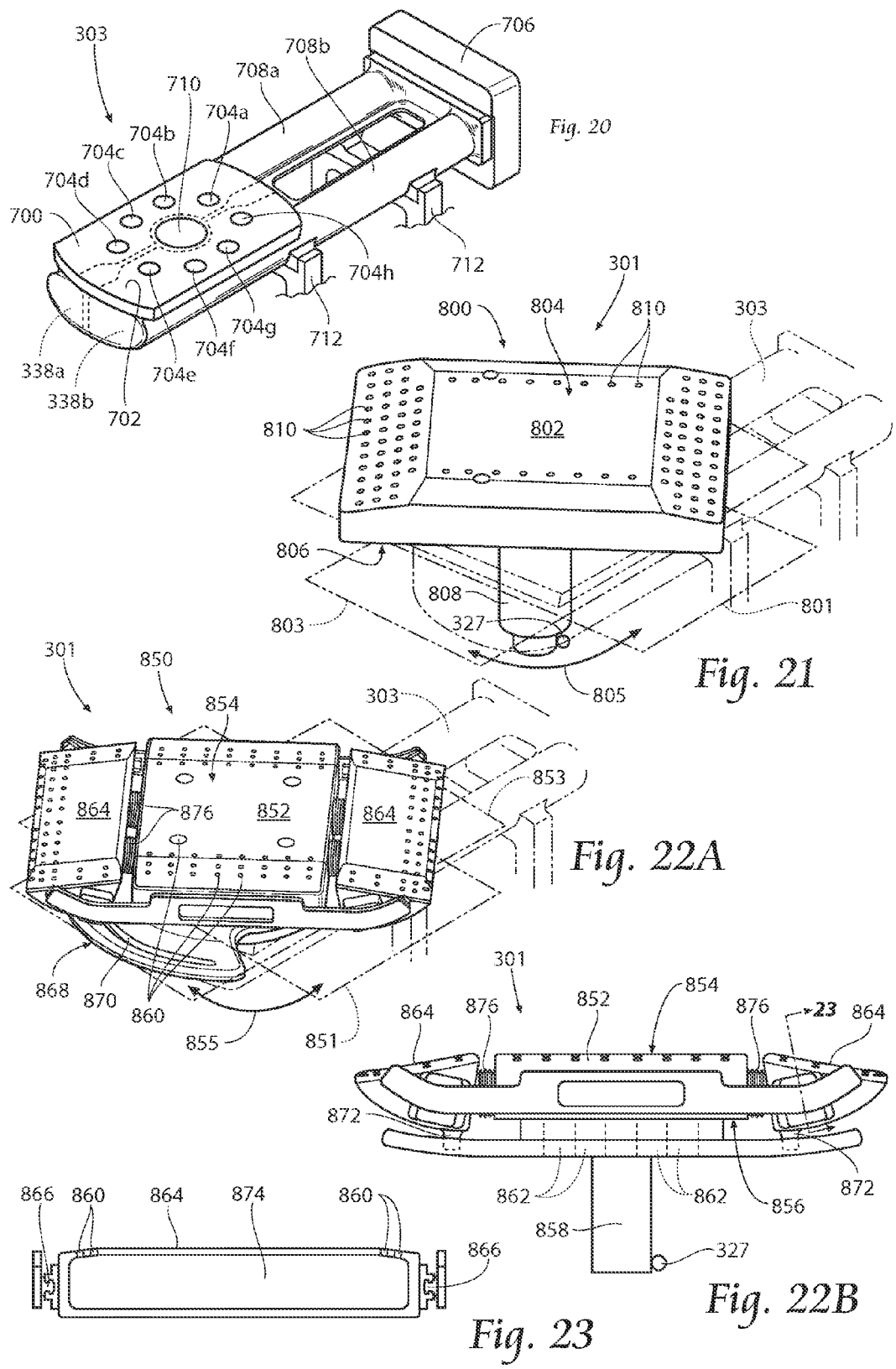

SINGLE TRANSFER INSERT PLACEMENT METHOD AND APPARATUS

RELATED APPLICATIONS

This application claims the benefit of U.S. Provisional Patent Application Ser. No. 61/642,237, filed 3 May 2012, and is a continuation-in-part of U.S. patent application Ser. No. 13/178,104, filed 7 Jul. 2011, which is a division of U.S. patent application Ser. No. 12/070,879, filed 21 Feb. 2008, now U.S. Pat. No. 7,975,584, which claimed the benefit of U.S. Provisional Patent Application Ser. No. 60/902,477, filed 21 Feb. 2007, and entitled "Single Transfer Insert Placement Method and Apparatus."

BACKGROUND OF THE INVENTION

This invention relates to a method and apparatus for receiving and cutting a continuous web, and transferring articles, or inserts, such as absorbent pads cut from the web in the manufacture of disposable absorbent articles such as diapers, incontinence control garments or female sanitary pads as they advance along a production line.

In the production and manufacture of disposable products such as sanitary napkins or pants-type diapers, it frequently becomes necessary to manufacture a component of the product in one orientation, and then to spin that component part to a predetermined angle, which is suitably oriented for use in another step in the production process. Various devices have been developed for this purpose and are known to those experienced in the industry. Examples of such apparatus are those described in U.S. Pat. Nos. 4,726,876, 4,880,102, and 5,025,910.

As mentioned above, a typical article or web to be reoriented by the apparatus of this invention is an absorbent pad. Past devices normally cut a received web to form the pad prior to placement on a transfer mechanism. Cutting the web to form the pad prior to placement on the transfer mechanism requires a separate step between the cutting process and transfer process. Therefore, it is desirable to have an apparatus for receiving a continuous web onto a transfer mechanism prior to cutting the web into discrete pads, cutting a section from the web thereby forming a pad, spinning the pad to a predetermined angle, and transferring the pad for placement on a receiving surface, thereby eliminating the requirement of a separate transfer step between the cutting and transferring step.

In addition to requiring spin, the web may be provided at one velocity and a pad may be cut from the web at a cut pitch. However, the cut pitch is likely a different spacing interval than the desired placement pitch on a receiving surface. In the case of a diaper, for example, the pad may be an absorbent insert to be placed on a fluid impervious chassis. Therefore, the web may be cut at a cut pitch, X, and the receiving pitch, or distance between consecutive chasses at the receiving surface may be represented as Y, where Y is comprised of a chassis trailing edge, an interval space, and a subsequent chassis leading edge. Therefore, it is desirable to compensate for the difference between the cut pitch, X, and the receive pitch, Y. Re-pitching is known in the art, but prior art device techniques tend to cause excessive wear on the devices due to the momentum changes that are required.

Hence, the art would benefit from an apparatus which is capable of receiving a continuous web at one velocity and cutting a section from the web at a first pitch to create a pad, which is transferred, oriented and properly spaced to a desired receiving pitch for placement on a receiving surface, while at the same time reducing wear on the devices.

SUMMARY OF THE INVENTION

Briefly, in accordance with a preferred embodiment thereof, provided are an apparatus and a method for receiving a continuous web, separating a section from the web thereby forming a pad, spinning the pad to a predetermined angle, and changing the spacing between neighboring pads while transferring the pad to a receiving surface.

In a preferred embodiment of the present invention, the apparatus generally includes a transfer mechanism and a cutter. The transfer mechanism comprises a plurality of pucks rotatably driven about a transfer axis. The cutter comprises an anvil roller and a plurality of knife blades rotatably driven about a knife blade axis. The transfer axis and knife blade axis are offset, so as to allow modification of the circumferential spacing between neighboring pucks. The pucks are each supported by a puck support. Each puck is coupled to a spin cam and a pitch cam. As the puck rotates about the transfer axis, the cams alter the position of the puck. The spin cam alters puck motion about a puck spin axis which is generally perpendicular to the transfer axis. The pitch cam alters the relative circumferential spacing of adjacent pucks.

A single transfer placement method according to the present invention includes the following steps:
1. Receiving a continuous web.
2. Cutting a discrete section from the continuous web, thereby forming a pad, wherein the pad is supported by a first surface; and
3. Transporting the pad on the first surface to a receiving surface.

Additionally the transporting step may incorporate the following steps:
1. Spinning the first surface to a predetermined angle; and
2. Changing the speed of the first surface.

In a further preferred embodiment of the present invention, a web cutting system is provided for use with a single transfer insert placement mechanism having at least one puck for transferring a discrete web and a continuous web feeding mechanism for feeding a continuous web wherein first and second rollers having substantially parallel axes and being aligned with one another form a nip at their juncture, an anvil is attached to one of the first and second rollers, a die is attached to the other of the first and second rollers, at least one vacuum source is coupled to one of the first and second rollers, a plurality of vacuum apertures is formed in the same roller and one of the first and second rollers is positioned adjacent to the single transfer insert placement mechanism and to the continuous web feeding mechanism whereby the continuous web is applied to the roller having the vacuum source coupled thereto and at least one discrete web is transferred from the puck to the same roller. The web cutting system may further include at least one compression roller, the compression roller positioned downstream of the nip. The web cutting system may further include a waste vacuum, the waste vacuum positioned adjacent the roller having the vacuum source coupled thereto. The web cutting system may further include the roller having the vacuum source coupled thereto having an anvil attached thereto. The web cutting system may further include apertures on the roller having the vacuum source coupled thereto and the apertures being segregated into first and second vacuum zones. The web cutting system may include the apertures on the roller having the vacuum source coupled thereto being segregated into a plurality of vacuum zones. The web cutting system may further include the vacuum source coupled to the first vacuum zone being different from the vacuum source coupled to the second vacuum zone. The web cutting system may further include a plurality of dies attached to one of the first and second rollers. The web cutting system may further include a plurality of anvils attached to one of the first and second rollers. The web cutting system may also further include the die being one or more knives.

Another preferred embodiment of the present invention is a web cutting system for use with a single transfer insert placement mechanism having at least one puck for transferring a discrete web and a continuous web feeding mechanism for feeding a continuous web including first and second rollers having substantially parallel axes and being aligned with one another to form a nip at their juncture, the first roller being an anvil roller, the second roller being a die roller, at least one vacuum source being coupled to one of said first and second rollers, a plurality of vacuum apertures formed in the same roller and one of the first and second rollers positioned adjacent to the single transfer insert placement mechanism and to the continuous web feeding mechanism whereby the continuous web is applied to the roller having the vacuum source coupled thereto and at least one discrete web is transferred from the puck to the same roller.

DESCRIPTION OF THE DRAWINGS

FIG. 18A is a perspective view of a preferred pitch cam follower cartridge.

FIG. 18B is a perspective partial assembly view of a preferred pitch cam follower cartridge being installed on a preferred puck wheel.

FIG. 19 is a perspective view of a preferred method of rotating a vacuum manifold.

FIG. 20 is a perspective view of a preferred puck support according to the present invention.

FIG. 21 is a perspective view of a first preferred puck according to the present invention.

FIG. 22A is a perspective view of a second preferred puck according to the present invention.

FIG. 22B is a side elevation view of the puck of FIG. 22A.

FIG. 23 is a cross-section view taken along line 23-23 of FIG. 22.

FIG. 35b is a side elevation view of the roller of FIG. 35a.

FIG. 35c is a top plan view of the roller of FIG. 35a.

DETAILED DESCRIPTION

Although the disclosure hereof is detailed and exact to enable those skilled in the art to practice the invention, the physical embodiments herein disclosed merely exemplify the invention, which may be embodied in other specific structures. While the preferred embodiment has been described, the details may be changed without departing from the invention.

Figure 1:
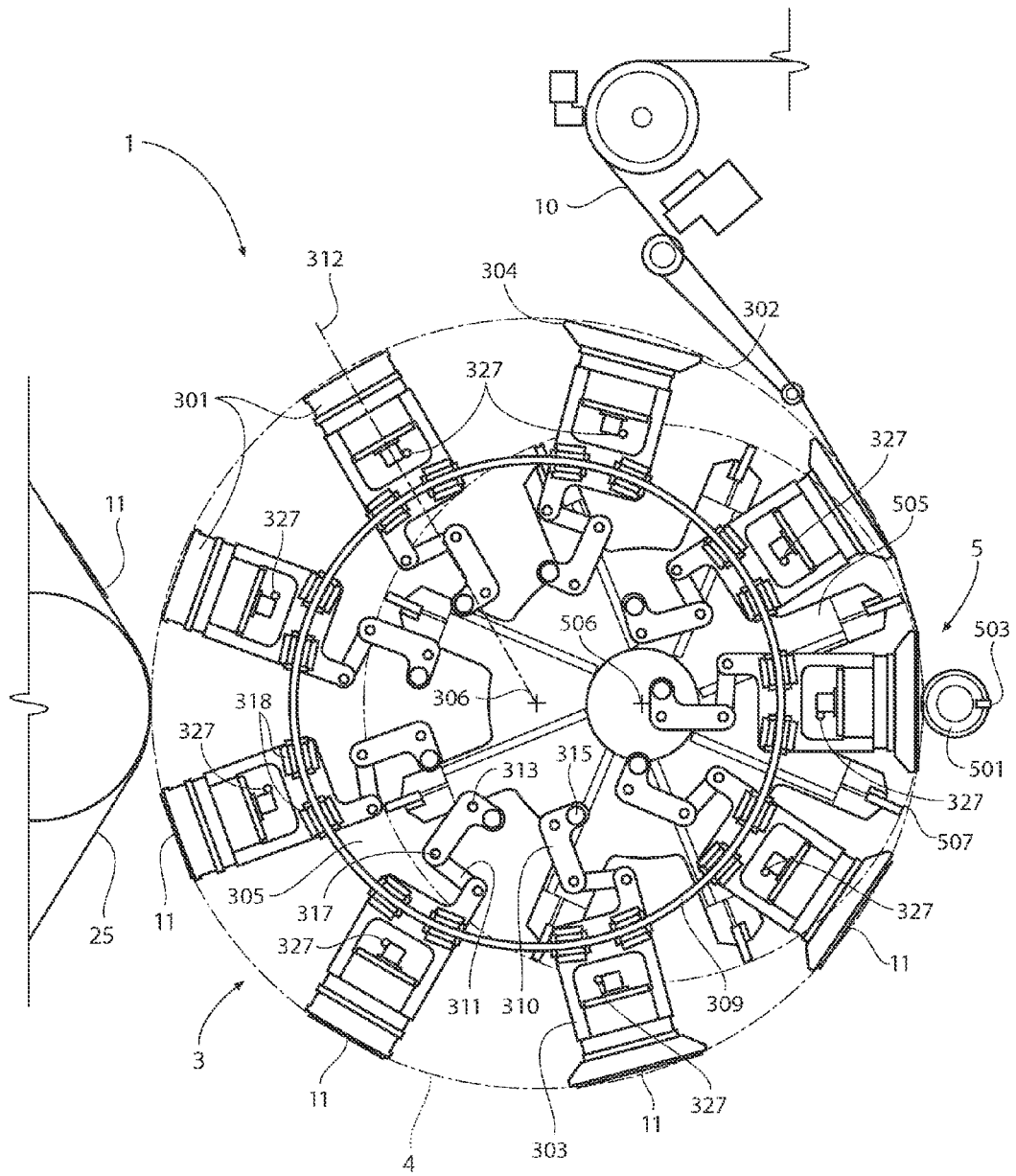
FIG. 1 is a front elevation view of an embodiment of a system according to the present invention.

Turning now to the drawings, FIG. 1 illustrates a front elevation view of a first embodiment 1 of an apparatus according to the present invention. The apparatus 1 preferably includes a transfer mechanism 3 and a cutter 5.

Figure 2:
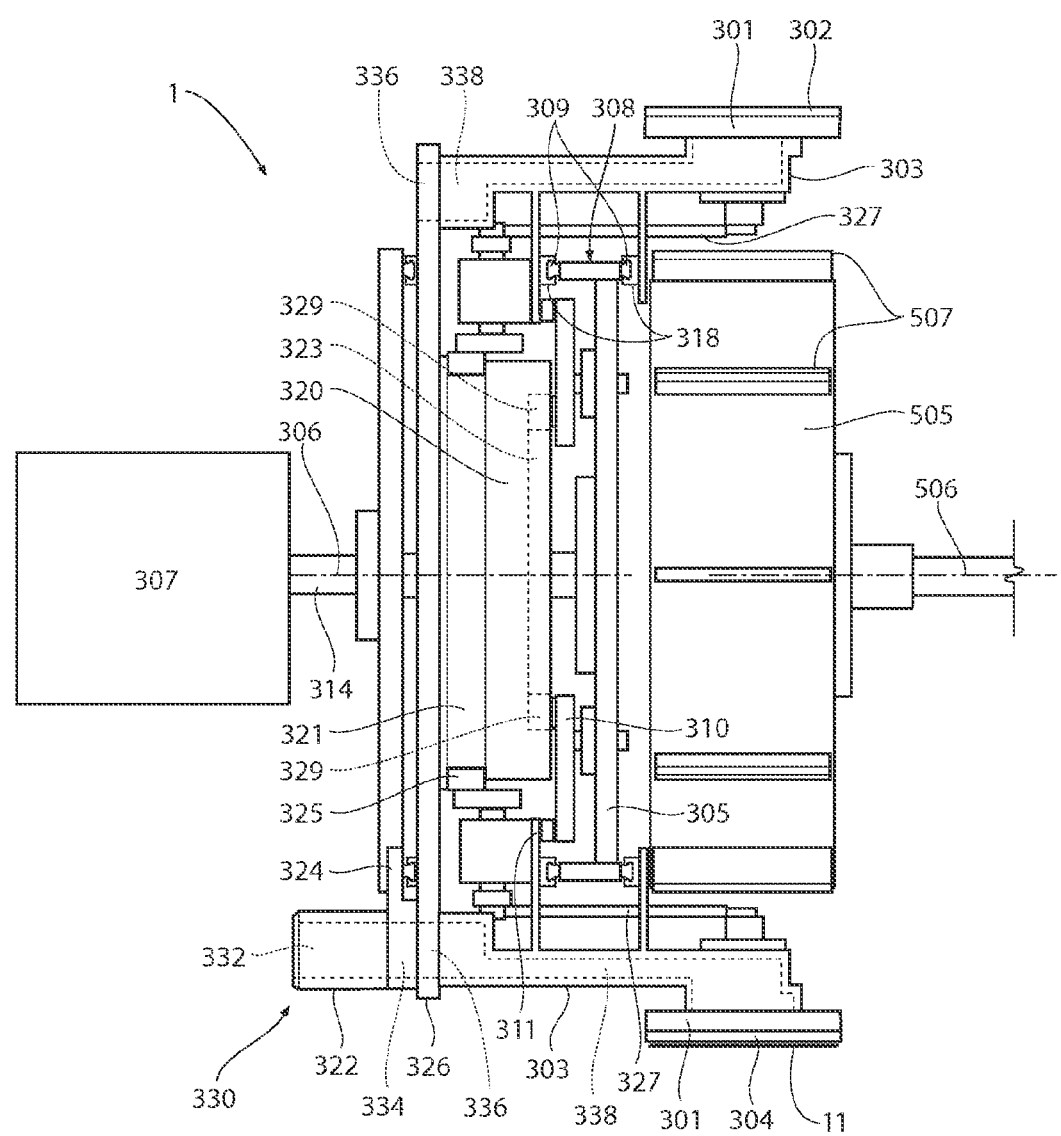
FIG. 2 is a right side elevation view of the embodiment in FIG. 1, eliminating components that would otherwise obstruct the desired view, namely multiple pucks and anvil roll.
Figure 3:
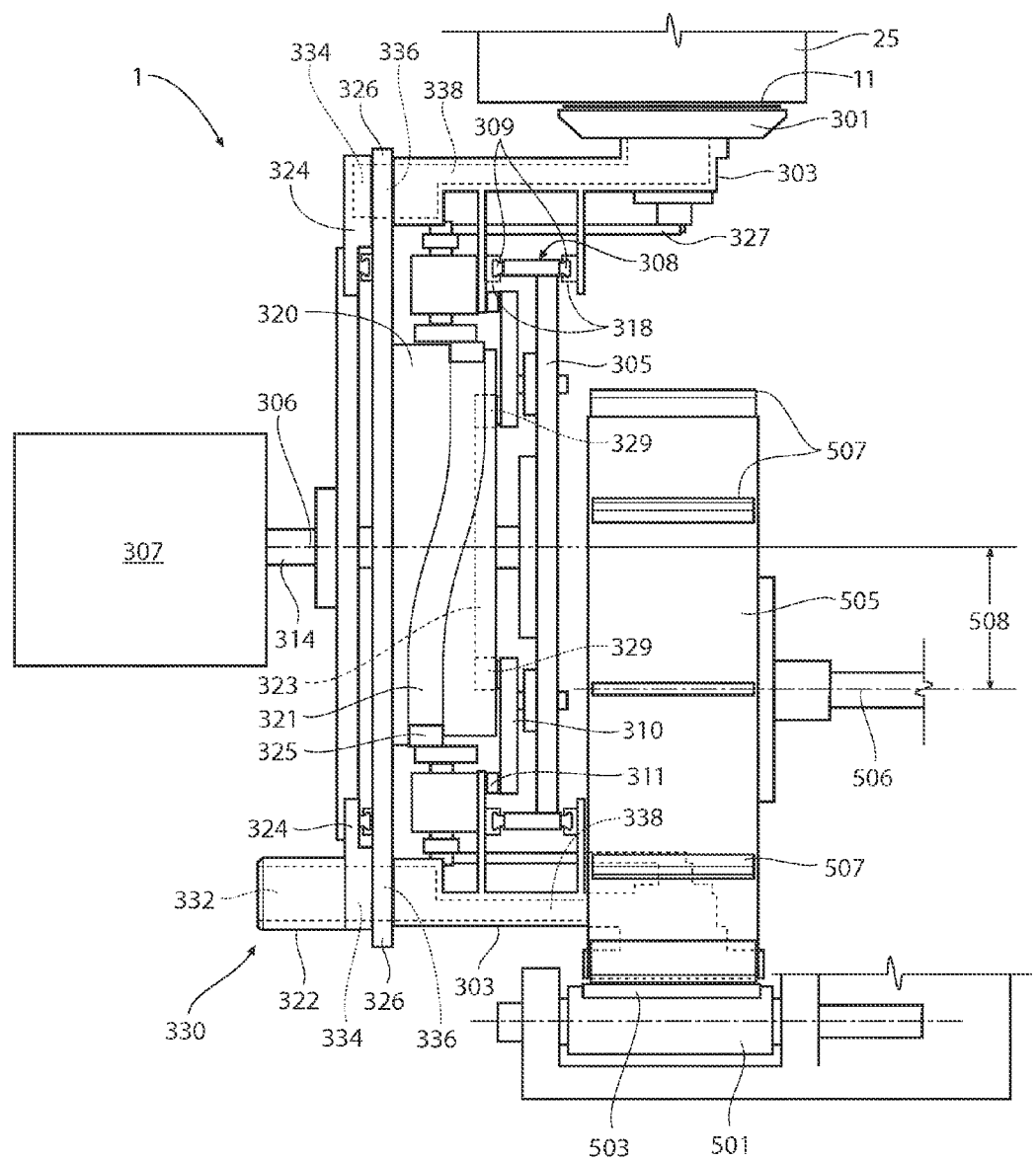
FIG. 3 is a top plan view of the embodiment in FIG. 1, eliminating components that would otherwise obstruct the desired view, namely multiple pucks.

Referring, in addition to FIG. 1, to FIGS. 2 and 3, the transfer mechanism 3 includes a plurality of pucks 301. Each puck 301 has a leading edge 302 and a trailing edge 304 and is coupled to a puck support 303, which is ultimately rotated by a puck wheel 305 about a puck transfer axis 306, which is a major axis of rotation, through a transfer path 4. As used throughout the description of the preferred embodiment, "rotate" and its variants refer to the movement of an entire puck 301 and puck support 303 assembly about the transfer axis 306, while "spin" and its variants refer to the radial spin of a puck 301 about a puck spin axis 312, which is substantially perpendicular to the puck transfer axis 306. The puck wheel 305 is driven preferably by a substantially operationally constant rotational force provided by a shaft 314 coupled to a motor 307.

The puck support 303 is coupled to the puck wheel 305 by a primary pitch linkage 310 and a secondary pitch linkage 311. The primary pitch linkage 310 preferably includes three attachment points; a puck wheel anchor 313, a pitch cam follower anchor 315, and a secondary linkage anchor 317. The puck wheel anchor 313 couples the primary pitch linkage 310 to a predetermined location on the puck wheel 305. The puck wheel anchor 313 serves as a minor rotation axis about which the primary pitch linkage 310 rotates, thereby causing, in cooperation with the secondary pitch linkage 311, the associated puck 301 to change its position in relation to the major axis of rotation, the puck transfer axis 306. The pitch cam follower anchor 315 couples the primary pitch linkage 310 to a pitch cam follower 329. Finally, the secondary linkage anchor 317 couples the primary pitch linkage 310 to the secondary pitch linkage 311. The secondary pitch linkage 311 preferably provides a substantially linear link coupled near one end to the primary pitch linkage 310 and near the other end to the puck support 303.

To facilitate position modification of the pucks 301, the apparatus 1 also includes a cam plate 320 situated about the transfer axis 306. The cam plate 320 is preferably a stationary plate having at least two raceways therein or thereon, a spin cam race 321 and a pitch cam race 323. The spin cam race 321 is preferably provided around the outside edge of the cam plate 320. To achieve desired spin of the pucks 301, a spin cam follower 325, which is preferably a roller bearing, is in sliding or rolling communication with the spin cam race 321. A spin linkage 327 couples the puck 301 to the spin cam follower 325. While the spin cam race 321 is depicted as providing a ninety degree puck rotation, positioning of the spin cam race 321 is generally determined by the desired spin angle of the puck 301.

In addition to aiding puck spin, the cam plate 320 assists the pitch change, or altered circumferential puck spacing. The pitch change is accomplished by using the pitch cam follower 329, which is preferably a roller bearing, in sliding or rolling communication with the pitch cam race 323. Located preferably near a radial distal edge 308 of the puck wheel 305 is a pair of pitch rails 309, which allow controlled circumferential displacement of the pucks 301. The pitch rails 309 are preferably fastened to the puck wheel 305. The puck support 303 is provided with rail guides 318, which are slidably disposed on the pair of pitch rails 309.

The pitch cam race 323 is formed, preferably on a face of the cam plate 320, to effect a desired pitch change. Although different designs could be employed, where the pitch cam race 323 is situated further from the puck transfer axis 306, the velocity of the puck 301 will be higher than where the pitch cam race 323 is positioned nearer the transfer axis 306. As described in this preferred embodiment, the maximum pitch change, therefore, is generally determined by the shape of the pitch cam race 323 and the combined length from the primary pitch linkage 310 of the puck wheel anchor 313 to the secondary pitch linkage 311 end which is coupled to the puck support 303.

The cutter 5 is best described with reference to FIGS. 1 and 3. The cutter 5 preferably comprises an anvil roller 501 having an anvil surface 503, and a knife wheel 505. The knife wheel 505 includes a plurality of knife blades 507 radially disposed about a knife wheel axis 506. The knife wheel 505 preferably has fewer blades 507 than the number of rotator pucks 301 provided on the transfer mechanism 3. The fewer number of blades 507 provided allows a greater offset 508 between the knife wheel axis 506 and the puck transfer axis 306. The eccentric offset 508 causes a virtual withdrawal of the knife blades 507 to allow more space to achieve desired pitch change. Alternatively, an anvil wheel having a plurality of anvils could be substituted for the knife wheel 505 and a knife roller having a knife blade could be substituted for the anvil roller 501.

Figure 4A:
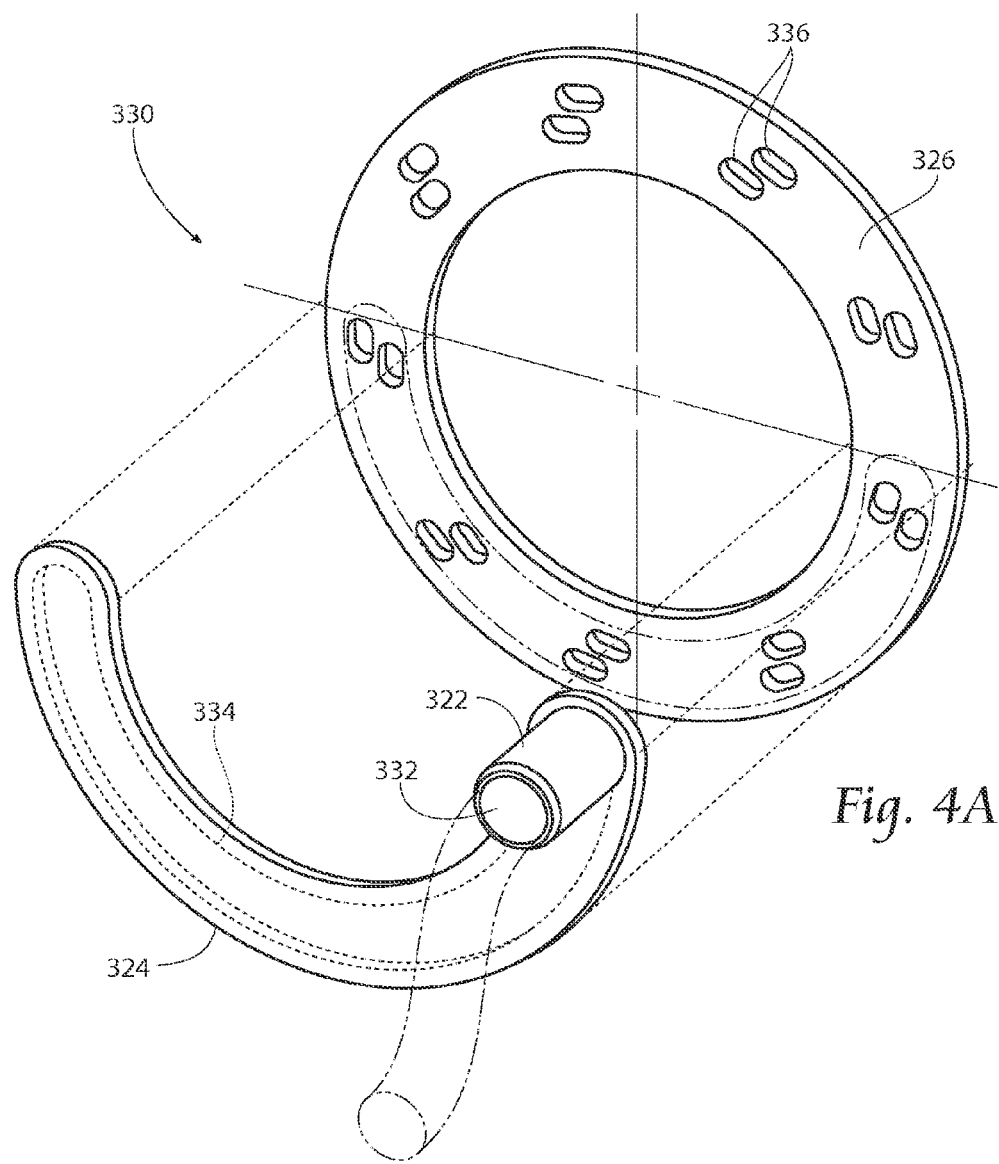
FIG. 4A is a perspective view of a stationary vacuum manifold and rotating vacuum manifold utilized by the embodiment FIG. 1.

As seen in FIG. 4A, the apparatus 1 may also include a manifold 330 to allow fluid communication between a vacuum supply (not shown) and the pucks 301 at certain positions. The manifold 330 is preferably comprised of a vacuum port 322, a stationary vacuum manifold 324 and a rotating vacuum manifold 326. The vacuum port 322 preferably provides vacuum connection point, which may be standard or custom. The port 322 provides a support structure and an aperture 332 to allow vacuum pressure to be drawn through the port 322. The stationary vacuum manifold 324 is generally a fixed plate having at least one vacuum groove 334 formed therethrough at a predetermined location. The vacuum groove 334 is stationary and in fluid communication with the vacuum port aperture 332. The rotating vacuum manifold 326 is generally a rotating plate preferably having a face in slidable relation to the puck supports 303. The rotating manifold 326 includes at least one aperture 336 to allow, when in fluid communication with the aperture 334 in the stationary manifold 324, a vacuum to be drawn through the vacuum port 322, the stationary manifold 324, the rotating manifold 326, the puck support 303 and the puck 301.

Figure 4B:
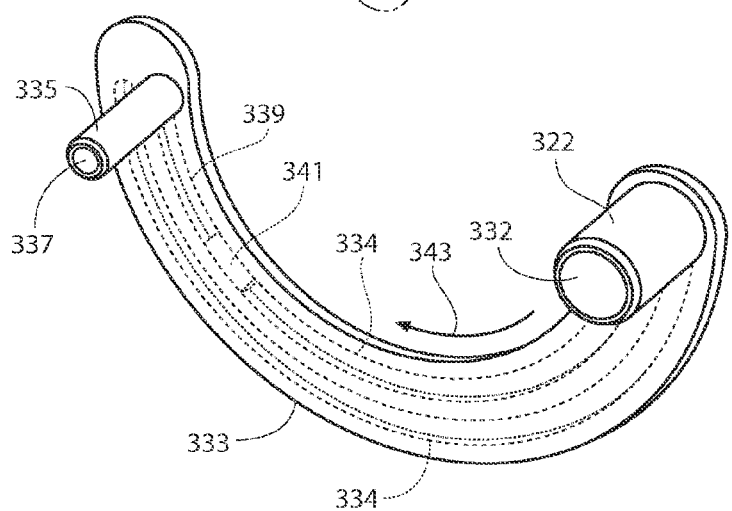
FIG. 4B is a perspective view of an alternate stationary vacuum manifold.

FIG. 4B provides an alternate stationary vacuum manifold 333. This embodiment 333 preferably includes a vacuum port 322 coupled to a vacuum source (not shown) and interfaces to a rotating vacuum manifold, such as the rotating vacuum manifold 326 in FIG. 4A or FIG. 19. The vacuum port 322 preferably provides vacuum connection point, which may be standard or custom. The port 322 provides a support structure and an aperture 332 to allow vacuum pressure to be drawn through the port 322. The stationary vacuum manifold 333 is generally a fixed plate having at least one, but preferably two vacuum grooves 334 formed at predetermined locations. The vacuum grooves 334 are in fluid communication with the vacuum port aperture 332. The manifold 333 also preferably includes an ejection port 335 including an ejection aperture 337, which may be adapted to be coupled to a compressed air source (not shown). The ejection port 335 is preferably in fluid communication with an ejection groove 339, which may be an extension of one of the vacuum grooves 334, but separated therefrom by a vacuum plug 341. The vacuum plug 341 may be selectively placeable but is preferably stationarily held in one of said vacuum grooves 334. In this way, vacuum may be drawn through the vacuum grooves 334 and compressed air may be forced through the ejection port 335 and into the ejection groove 339. As the rotating manifold 326 rotates in a first direction 343, a pair of manifold apertures 336 may each encounter a vacuum groove 334, perhaps substantially simultaneously. However, it may be desirable to remove vacuum from one of the apertures 336 and then force air through that same aperture 336 in opposite direction to the vacuum to aid in the transfer of a pad 11 to a receiving surface 25. For instance, it may be desirable to maintain vacuum on the trailing edge of a puck 301 while forcing a pad 11 off of the puck 301 leading edge with compressed air provided through the ejection aperture 337 and ejection groove 339.

Although the terms "circumferential" and "rotation" are used to describe the transfer movement of the pucks 301, it is to be understood that the invention is not limited to applications utilizing a circular motion. For instance, rather than be driven by a puck wheel 305 rotated by a motor 307, the pucks 301 may be coupled to a chain drive (not shown) or something similar. The travel path of the pucks 301 may then be defined by the shape of an employed cam plate 320 or by the path of any supporting pitch rails 309 used.

All of the components of the apparatus 1 are either generally well known in the art, such as the roller bearings preferred for the cam followers, or can readily be made of standard materials. For example, the knife blades 507 and anvil roll 501 may be made of well known materials such as common tool steels. The supporting and rotating structures, such as the puck supports 303, linkages, wheels, etc., may be made of suitable aluminum. The pucks 301 are formed from any desirable material, but a lightweight material is preferred, such as nylon.

The operation of the present apparatus 1 will be described next with reference to FIGS. 5-15, inclusive. Generally, the apparatus 1 receives a continuous web 10, separates a section from the continuous web 10 to form an insert or pad 11, spins the pad 11 to a predetermined angle, and changes the pitch between consecutive pads 11. While the operation of the apparatus 1 is described with reference to a single puck 301a and a single knife blade 507a, it is to be understood that the operation of the remaining pucks 301 and knife blades 507 is at least substantially similar. Furthermore, although the operation is described with reference, in FIGS. 8-15, to discrete puck positions P1-P8, it is to be understood that the operation is preferably generally continuous. The discrete positions aid in illustrating the operations being performed.

Figure 5:
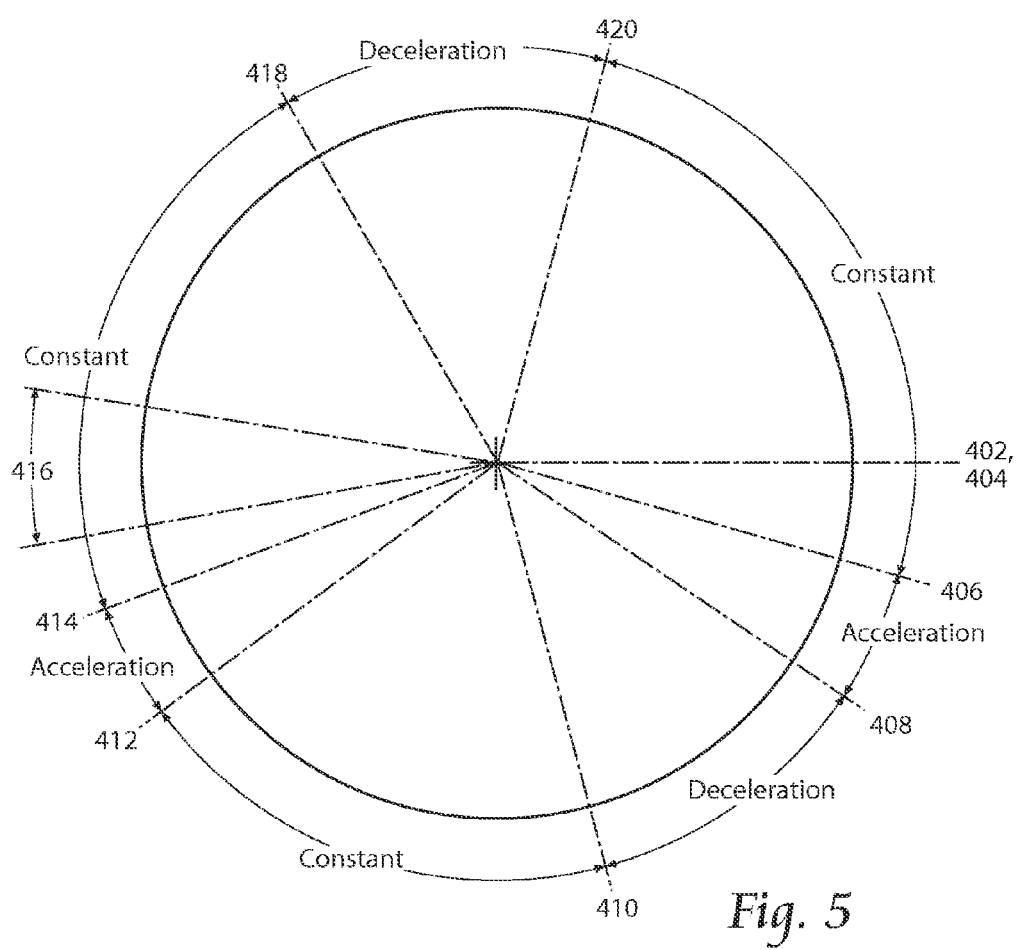
FIG. 5 is a front elevation schematic representation of a first preferred velocity profile of the apparatus of FIG. 1.
Figure 6:
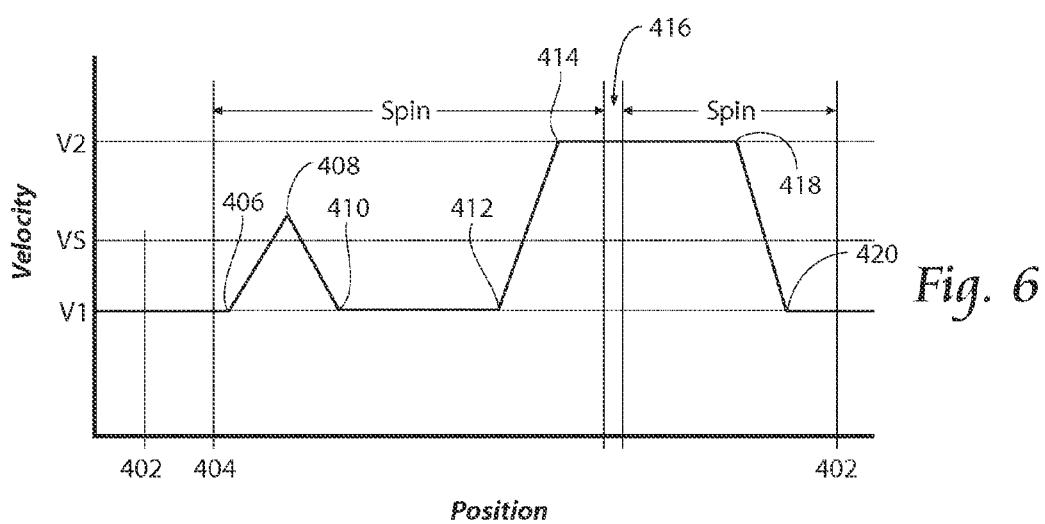
FIG. 6 is a graph view of the preferred velocity profile of FIG. 5.
Figure 7:
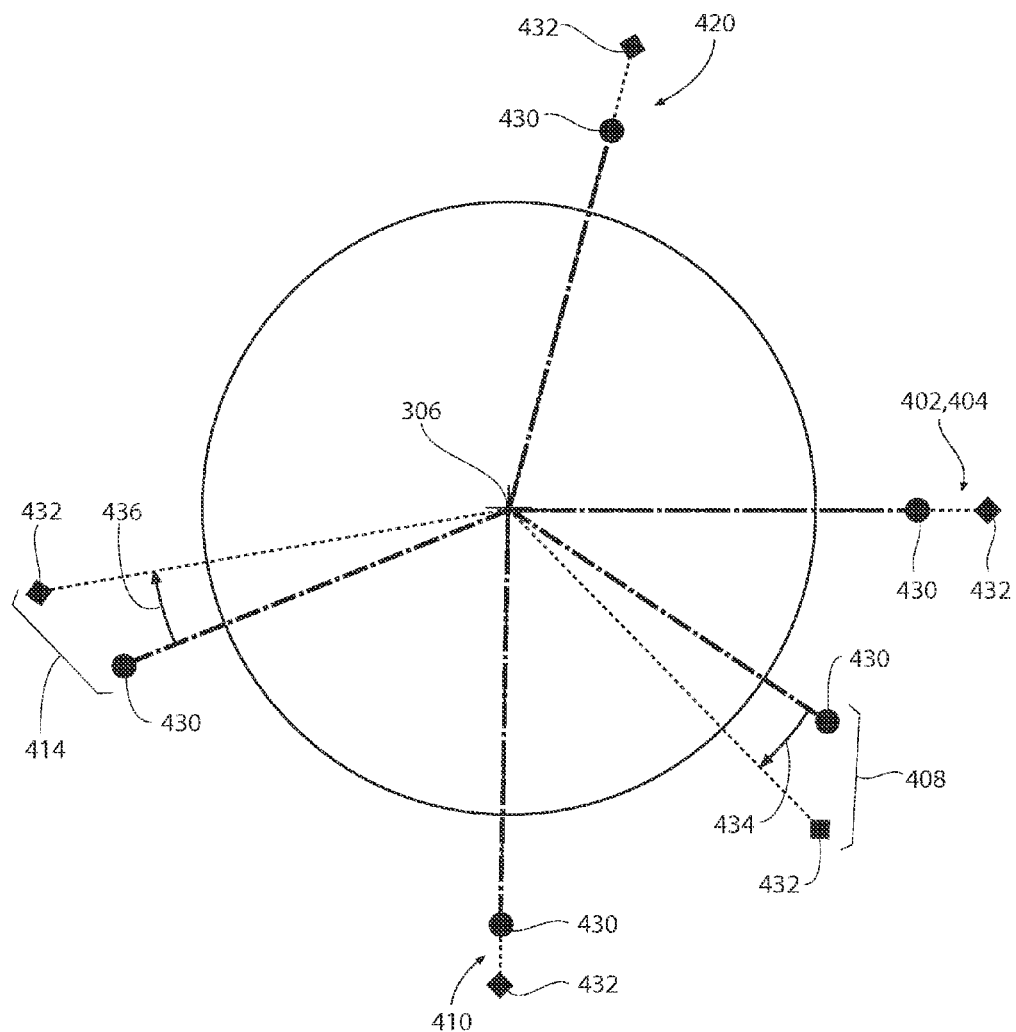
FIG. 7 is a front elevation schematic representation of puck position changing relative to a major axis of rotation, the puck following the velocity profile of FIG. 5.

FIGS. 5 and 6 depict a puck velocity profile, as each puck 301 rotates through various portions of its travel path. With reference also to FIG. 1, the puck transfer mechanism 3 rotates about the puck transfer axis 306 at a relatively constant velocity VS. When a puck 301 receives continuous web material 10, the puck 301 may be moving at a substantially constant first velocity V1. A pad 11 is then cut from the continuous web 10. To create the pad 11, a first cut 402 is made proximate the leading puck edge 302 and a second cut 404 is made proximate the trailing puck edge 304. Just after a pad 11 is cut from the web material 10, the puck 301 may be accelerated 406 to prevent any collision with the subsequent neighboring puck 301 and may be decelerated 408 thereafter back to a substantially constant velocity 410, which may be the first velocity V1. Sometime after the trailing edge cut 404 and prior to placement 416 of the pad 11 on a receiving surface 25, the puck 301 spins to a desired angle and the velocity of the puck 301 may change 412 to achieve a desirable predetermined circumferential spacing. Upon or after reaching a substantially constant 414 second velocity V2, the pad 11 is placed 416 on the receiving surface 25. After pad placement 416, the puck 301 is decelerated 418 to a substantially constant 420 first velocity V1 and is spun back to a web-receiving orientation. The process then begins anew.

During periods of acceleration and deceleration, the pucks 301 change position relative to the major axis of rotation, the puck transfer axis 306. This can best be seen by reference to FIG. 7. A first reference point 430 represents a point on the shaft (314 on FIGS. 2 and 3) spinning about the puck transfer axis 306 at the relatively constant velocity VS during operation of the device 1. A second reference point 432 represents a position of a puck 301. While the shaft reference 430 may be rotating about the puck transfer axis 306 at a constant velocity, the position of the puck reference 432 with respect to the shaft 314 may change a desirable amount, such as an increase of ten degrees or more of rotation during acceleration and a decrease of ten degrees or more of rotation during deceleration. To illustrate, the shaft reference 430 is generally radially aligned with the puck reference 432 during times of cutting 402,404. At the end 408 of the first acceleration, the puck reference 432 has changed position relative to the shaft reference 430 by a first distance 434. At the end 410 of the first deceleration period, the references 430,432 are again aligned. Prior to pad placement 416, the puck 301 is again accelerated, and at the end 414 of the second acceleration the puck reference 432 has advanced beyond the shaft reference 430 by a second distance 436. The first distance 434 may be the same as, or different than, the second distance 436. Finally, at the end 420 of the second deceleration period, both references 430,432 are aligned and ready for another revolution.

Figure 8:
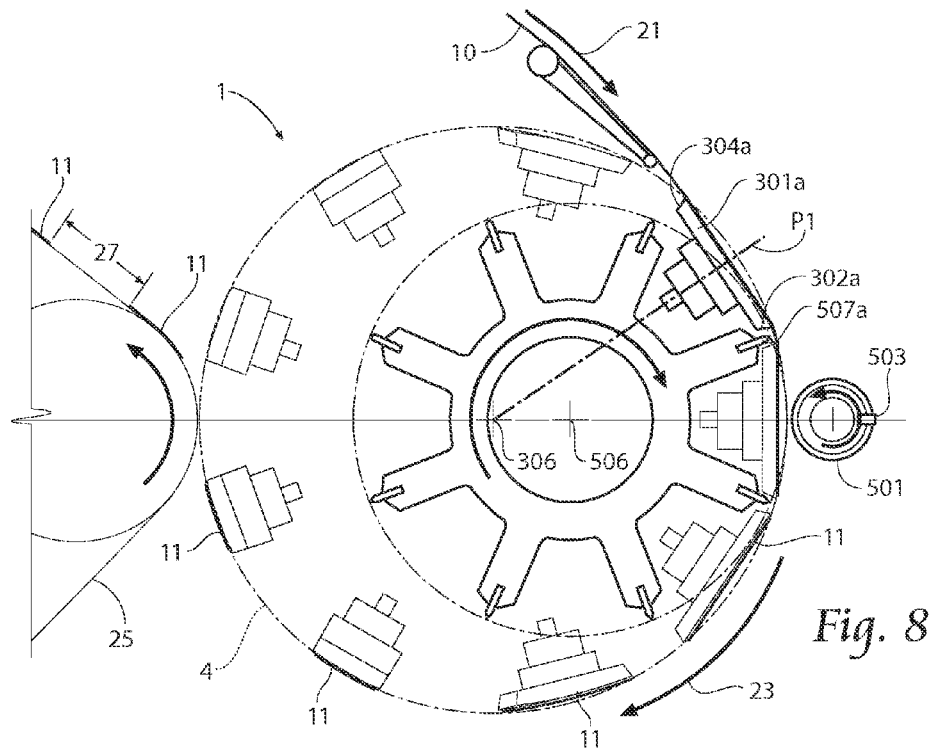
FIG. 8 is a front elevation view of the embodiment in FIG. 1 in a first position, eliminating some detail to better illustrate functionality.

FIG. 8 shows a representative puck 301a in a first position P1. In the first position P1, the puck 301a receives continuous web material 10 traveling in a first direction 21 at the first velocity. A vacuum is drawn through the vacuum port 326, the stationary vacuum manifold 322, the rotating vacuum manifold 324, the puck support 303 and the puck 301a to support the material 10 on the puck 301a surface. While receiving the web 10, the puck 301a is traveling about a puck wheel axis 306 in a second direction 23, to which at this point P1 the first direction 21 is preferably substantially tangential. The puck 301a continues to move in the second direction 23 into a second position P2.

Figure 9:
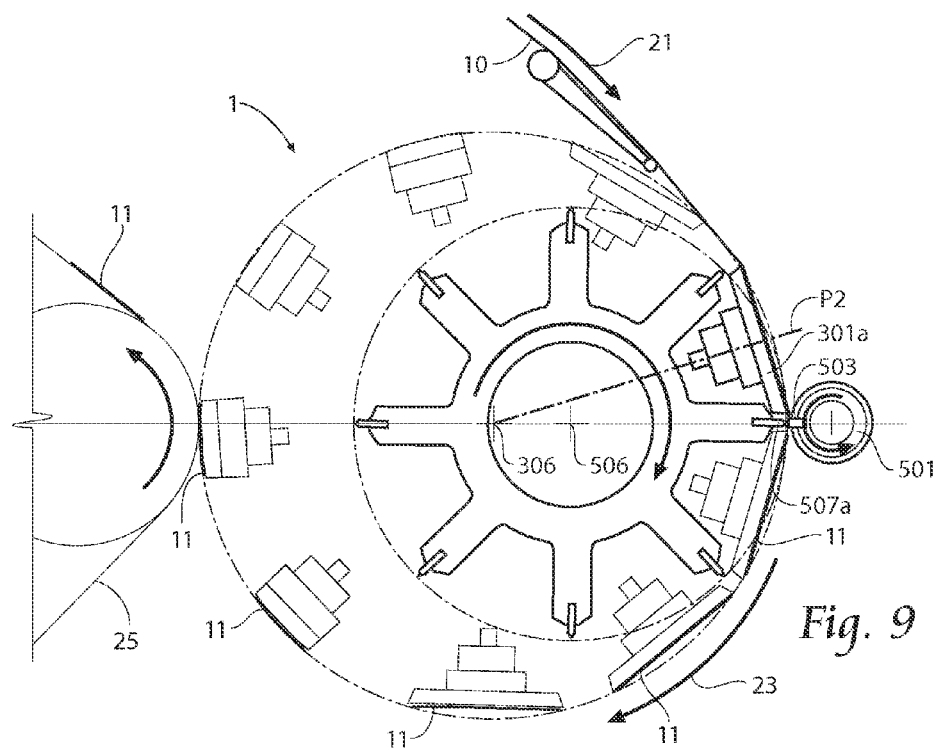
FIG. 9 is a front elevation view of the embodiment in FIG. 1 in a second position, eliminating some detail to better illustrate functionality.

FIG. 9 depicts the puck 301a in the second position P2. In this position, the puck 301a is at the leading edge cut time 402 of FIG. 6. Here, the cutter anvil surface 503 cooperates with a representative knife blade 507a to cut the web 10 proximate the leading edge 302a of the puck 301a. After receipt of the web 10 and the cut made near the leading edge 302a, the puck 301a proceeds to travel in the second direction 23 past the anvil roller 501 to a third position P3.

Figure 10:
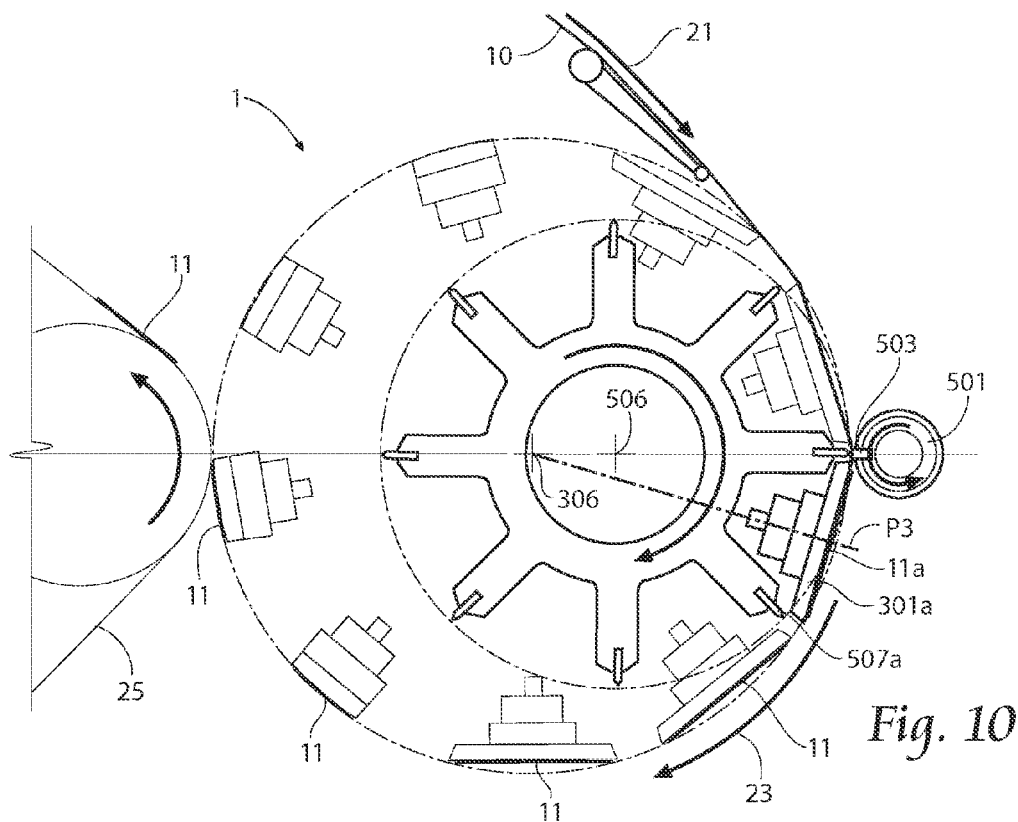
FIG. 10 is a front elevation view of the embodiment in FIG. 1 in a third position, eliminating some detail to better illustrate functionality.

FIG. 10 shows the puck 301a in the third position P3. In this position P3, the puck 301a is at the trailing edge cut time 404 of FIG. 6. In this position P3, the cutter anvil surface 503 cooperates with a knife blade 507 to cut the web 10 proximate the trailing edge 304a of the puck 301a to cut a section 11a from the web 10. The section 11a is held to the puck 301a by the vacuum, which was drawn previously. After the cut made near the trailing edge 304a, the puck 301a proceeds to travel in the second direction 23 to a fourth position P4.

Figure 11:
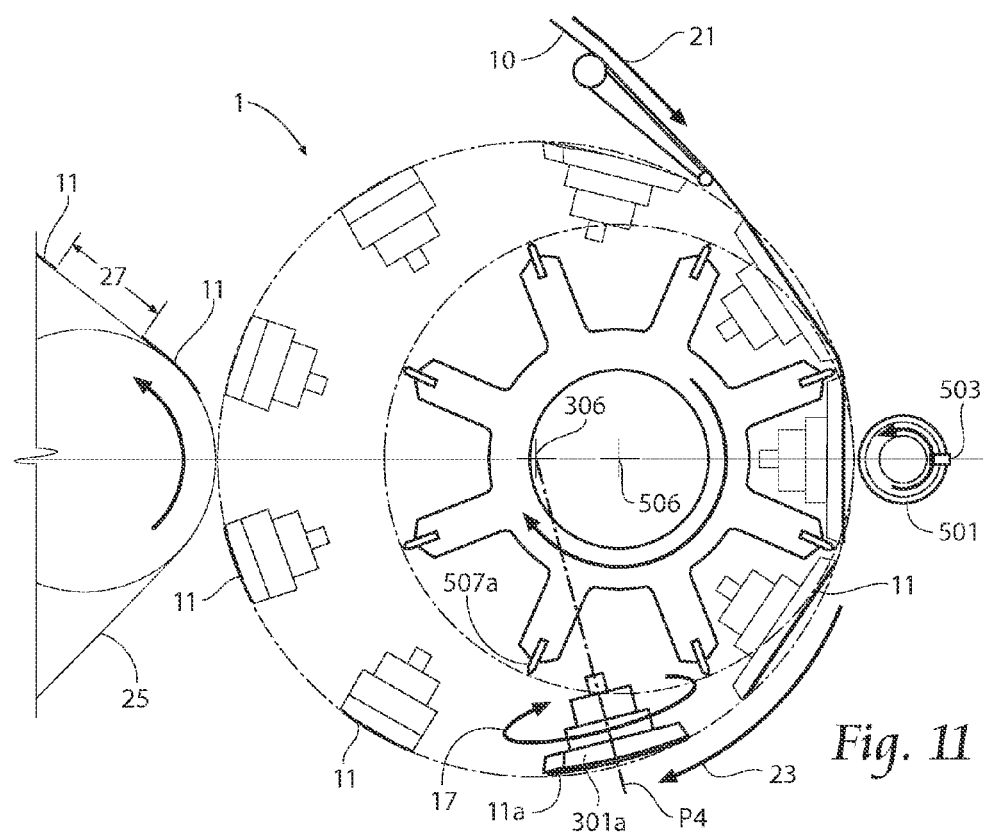
FIG. 11 is a front elevation view of the embodiment in FIG. 1 in a fourth position, eliminating some detail to better illustrate functionality.

FIG. 11 shows the puck 301a in the fourth position P4. As mentioned previously, it is often desirable to spin the cut section 11a to some predetermined angle prior to placement on a receiving surface 25. Here, the puck 301a is shown while in the midst of a spin. While FIG. 11 shows the puck 301a rotating in the fourth position P4, the puck 301a may rotate in a third direction 17 to a desired angle anytime after the trailing edge cut made at the third position P3 and before placement onto the receiving surface 25.

Besides rotation and spin of the pucks 301, the apparatus 1 may also change the circumferential spacing of the pucks 301a; thereby resulting in a placement pitch that is different from the pitch at which the web material 10 was cut. The eccentric nature of the puck wheel axis and the knife wheel axis 506 allows the puck 301a to drop away from the knife wheel 505, thereby providing greater angular movement ability than if a knife blade 507 remained between consecutive pucks 301. The ultimate circumferential spacing of the pucks 301 at the receiving surface 25 is a function of a desired placement pitch 27 and the speed at which the receiving surface 25 is traveling. In the preferred embodiment, the circumferential spacing is achieved by a desired pitch cam slot 323 configuration. Upon achieving desired circumferential spacing, the puck 301a arrives in a fifth position P5.

Figure 12:
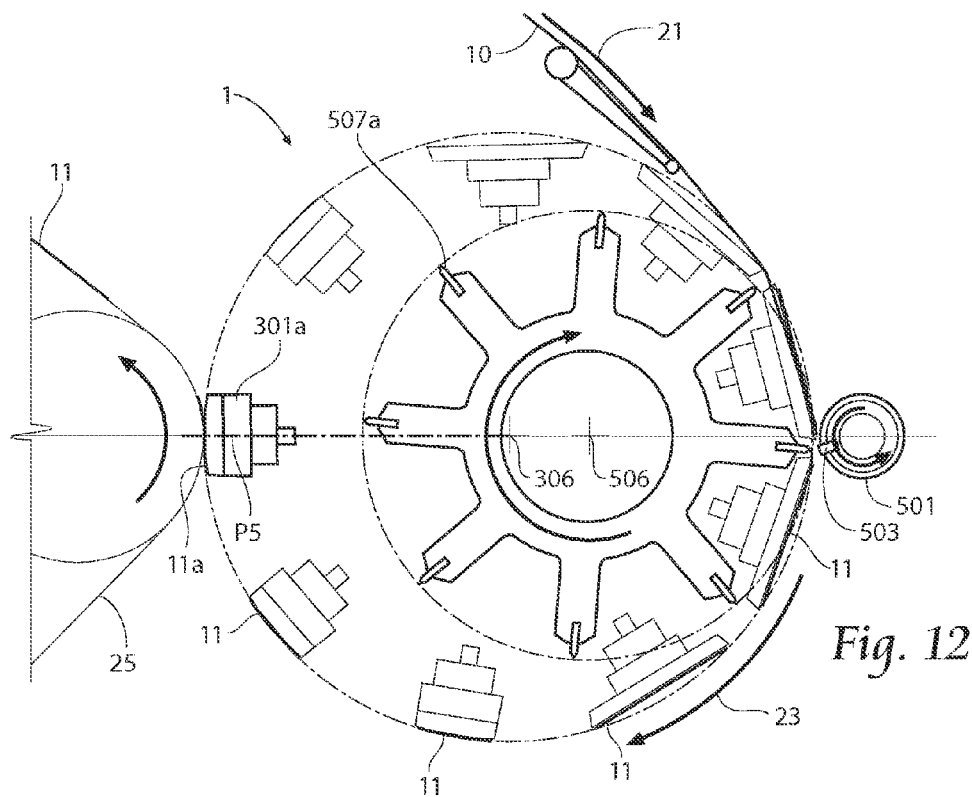
FIG. 12 is a front elevation view of the embodiment in FIG. 1 in a fifth position, eliminating some detail to better illustrate functionality.

The puck 301a is shown in the fifth position P5 in FIG. 12. In this position P5, the puck. 301a is at the middle of the placement time 416 shown in FIG. 6. The puck 301a has been situated at the correct placement pitch or distance 21 with respect to the puck 301 that preceded it 301a. At this pitch or distance 27, the section 11a is transferred to the receiving surface 25. At the time of placement, the vacuum that was drawn through the puck support 303 and puck 301a may be removed from at least a portion of the puck 301a, thereby allowing a smooth transfer of the cut insert 11a from die puck 301a to the receiving surface 25. The vacuum may remain active through die stationary vacuum manifold 322 and the rotating vacuum manifold 324 to assist in supporting subsequent sections 11 in place on later neighboring pucks 301. After placing the section 11a onto the receiving surface 25, the puck 301a continues in the second direction 23 to a sixth position P6.

Figure 13:
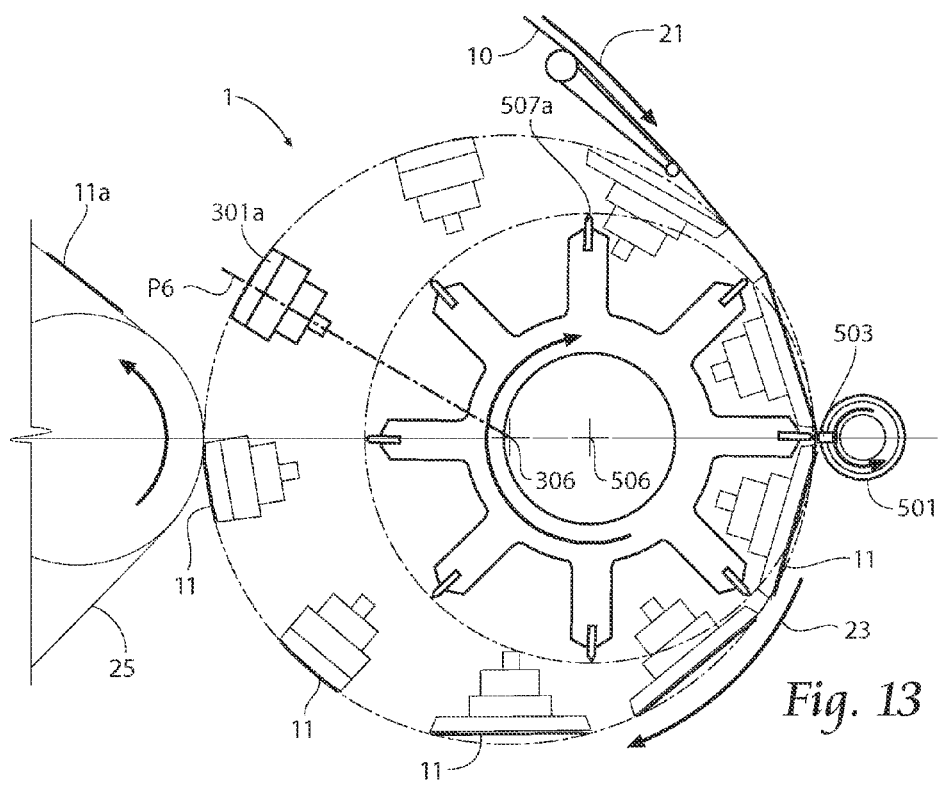
FIG. 13 is a front elevation view of the embodiment in FIG. 1 in a sixth position, eliminating some detail to better illustrate functionality.

FIG. 13 shows the puck 301a in the sixth position P6. The puck 301a is shown as having released the cut section 11a onto the receiving surface 25. The puck 301a continues to move in the second direction 23 to a seventh position.

Figure 14:
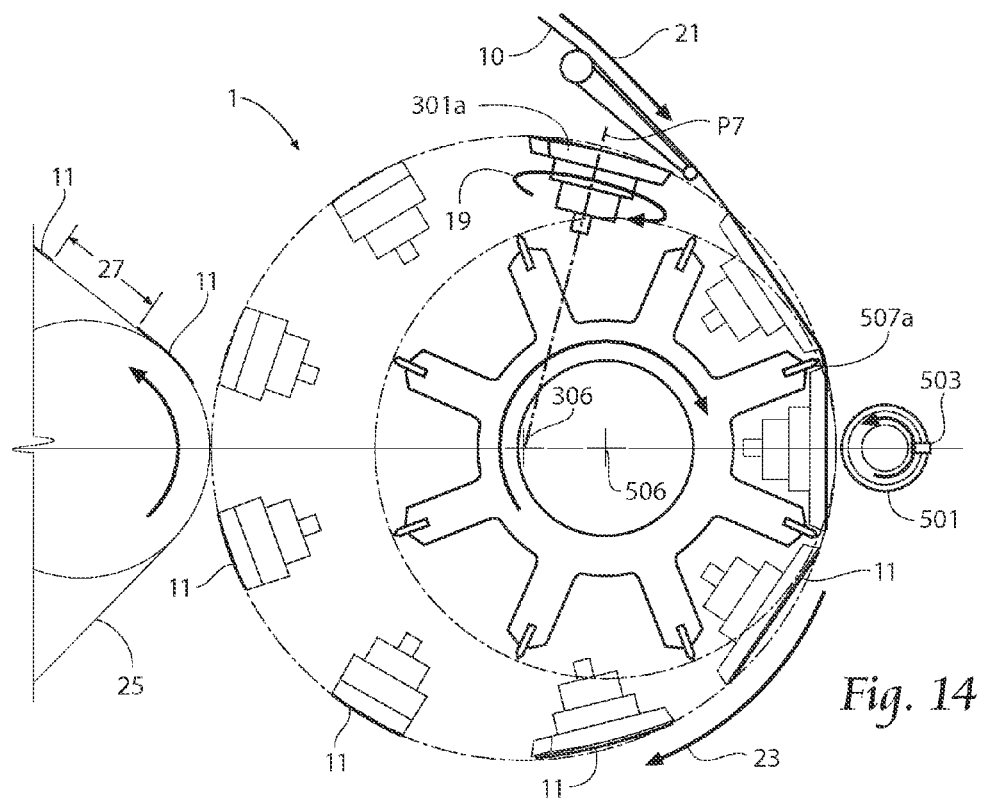
FIG. 14 is a front elevation view of the embodiment in FIG. 1 in a seventh position, eliminating some detail to better illustrate functionality.

FIG. 14 depicts the seventh position P7 of the puck 301a. If the puck 301a and pad 11a were rotated after cutting to some predetermined angle prior to placement on the receiving surface 25, the puck 301a may need to be adjusted to a web-receiving orientation. While FIG. 14 shows the puck 301a spinning in the seventh position P7, the puck 301a may spin in a fourth direction 19 anytime after the section 11a has been placed on the receiving surface 25 and before the continuous web 10 is received. The fourth direction 19 may be the same as the third direction 17 or different.

Figure 15:
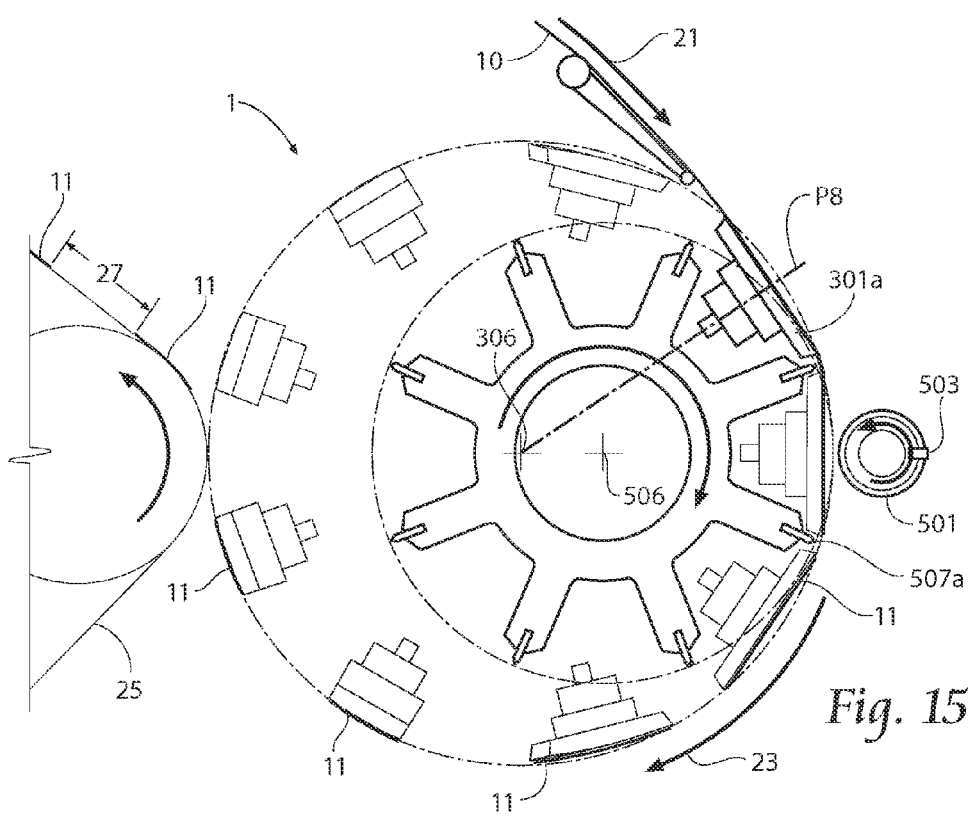
FIG. 15 is a front elevation view of the embodiment in FIG. 1 in an eighth position, eliminating some detail to better illustrate functionality.

Finally, the puck 301a is shown in the eighth position P8 in FIG. 15. The eighth position P8 is substantially similar to the first position P1, except that the knife blade 507a has now advanced a number of positions ahead of the puck 301a. The number of positions advanced is a function of the difference between the number of pucks 301 and the number of knife blades 507. In this operating example, there are nine pucks 301 and eight knife blades 507. Therefore, in the eighth position P8, the knife blade 507a has advanced one position ahead of its position in the first position P1.

Figure 16:
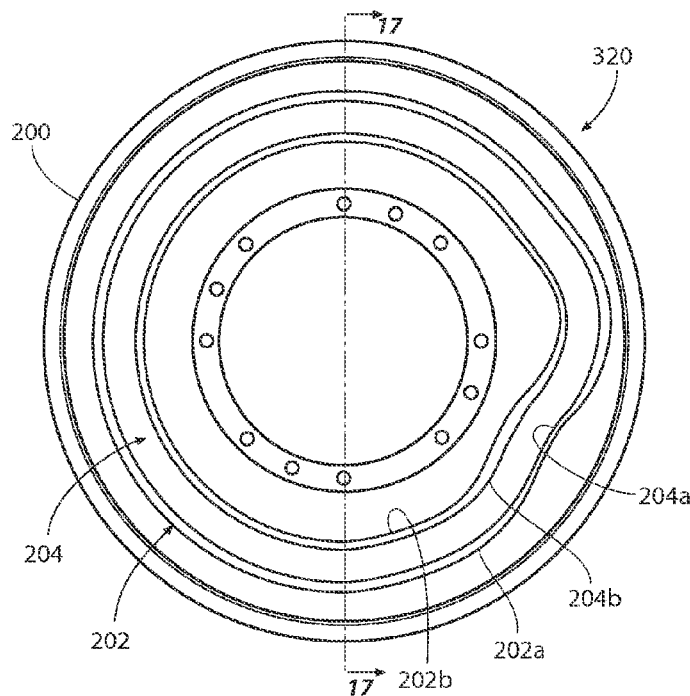
FIG. 16 is a rear elevation view of a preferred cam plate according to the present invention.

FIG. 16 depicts an alternative embodiment 200 of a cam plate 320 according to the present invention. The cam plate 200 preferably includes a spin cam race 321 and at least one pitch cam race 202, such as that formed by a first edge 202a and a second edge 202b, which are preferably concentric. This cam plate embodiment 200, however, more preferably includes a second cam race 204, which may be nested within the first 202 and formed by a third edge 204a and a fourth edge 204b, which are preferably concentric. Thus, a single replacement cam plate 200 may be used on different systems utilizing different static cam race profiles, thus reducing the number of spare parts that must be warehoused. Additionally, as further described below, a single cam plate 200 may provide added flexibility to a single machine if used in conjunction with pitch cam follower cartridges 600.

Figure 17A:
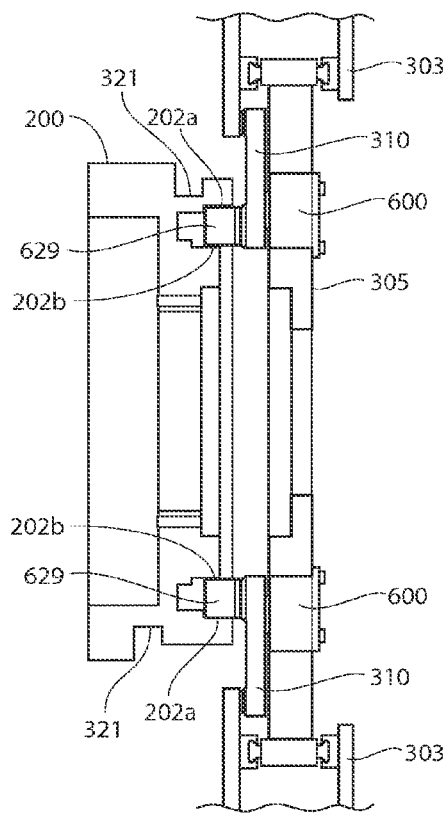
FIG. 17A is a right side elevation partial cutaway view of a system according to the present invention using a first cam profile of the cam plate of FIG. 16.
Figure 17B:
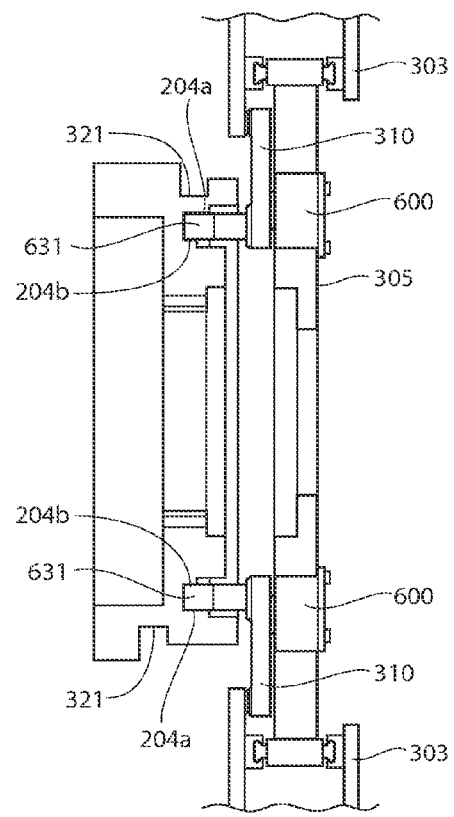
FIG. 17B is a right side elevation partial cutaway view of a system according to the present invention using a second cam profile of the cam plate of FIG. 16.

FIG. 17A and FIG. 17B show the use of the preferred cam plate 200 installed in a system according to the present invention and used in conjunction with pitch cam follower cartridges 600. FIG. 17A shows pitch cam follower cartridges 600 having a first pitch cam follower 629 sized and adapted to follow the first pitch cam race 202 in the cam plate 200. FIG. 17B shows pitch cam follower cartridges 600 having a second pitch cam follower 631 sized and adapted to follow the second pitch cam race 204 in the cam plate 200. While it will generally be desirable to utilize the same pitch cam race 202 or 204 to control the pitch of all pucks 301 in a given system, the invention does not preclude the use of the first pitch cam follower 629 with a first puck 301 and the second pitch cam follower 631 with a second puck on the same system. Furthermore, although only two pitch cam races 202,204 are disclosed, it is to be understood that further nesting of pitch cam races is possible, thus providing three or more nested cam profiles.

FIG. 18A is a perspective view of a preferred pitch cam follower cartridge 600. The preferred pitch cam follower cartridge 600 has a cartridge housing 602 having a first side 604 and a second side 606, each side having at least one but preferably a plurality of mounting flanges 608. The mounting flanges 608 on the first side 604 of a first cartridge 600 may be interlaceable with the mounting flanges 608 provided on the second side 606 of a second cartridge 600. Pivotally mounted to the cartridge housing 602 by a puck wheel anchor 313 is a primary pitch cam linkage 310. The pitch cam linkage 310 supports a pitch cam follower 329, such as the pitch cam follower 629 shown in FIG. 17A, and provides a site for a secondary linkage anchor 317.

FIG. 18B is a perspective partial assembly view of a preferred pitch cam follower cartridge 600 being installed on a preferred puck wheel 305. A plurality of fasteners 620 is provided to mechanically couple the pitch cam follower cartridges 600 to the puck wheel 305. The fasteners 620 may be threaded fasteners adapted to extend through the mounting flanges 608 on the cartridge housing 602 and cooperate with threaded apertures 622 on the puck wheel 305 to support the cartridge 600 on the wheel 305.

FIG. 19 is a perspective view of a preferred method of rotating a vacuum manifold 326. A drive pulley 650 is driven by a vacuum manifold drive shaft 652 and an endless belt 654 is placed about the drive pulley 650 and the vacuum manifold 326. An idler pulley 656 may be used to maintain desired tension of the belt 654. In this way, the rotating vacuum manifold 326 may be placed at variable positions relative to the main puck wheel 305. Such independent drive, may be advantageous for certain applications, such as offering size change flexibility.

FIG. 20 is a perspective view of a preferred puck support 303 according to the present invention. The puck support 303 comprises a puck support head 700 having a puck support surface 702. Extending through the puck support surface 702 is at least one, but preferably a plurality of vacuum apertures 704*a*-*h*. The puck support head 700 also preferably includes a bearing aperture 710 that extends through the head 700 at least substantially perpendicular to the puck support surface 702. Further, the puck support 303 is provided with rail interface arms 712, which preferably receive the rail guides 318 to interface with the pitch rails 309. The vacuum apertures 704*a*-*h* are in fluid communication with a vacuum chamber 338 that runs from the puck support head 700 through a puck support base 706 by way of vacuum pipes 708*a*,708*b*. While the puck support 303 may have a single vacuum chamber 338, the puck support 303 is preferably provided with two vacuum chambers 338*a*,338*b*. In this way, multiple apertures 704*a*-*d* may communicate with a first vacuum chamber 338*a*, which may be termed the leading vacuum chamber 338*a*. Further, multiple apertures 704*e*-*h* may communicate with a second vacuum chamber 338*b*, which may be termed the trailing vacuum chamber 338*b*. In operation, the cooperation of the puck support base 706 with the rotating vacuum manifold 326 and the stationary vacuum manifold 324 may desirably draw a vacuum through the leading vacuum chamber 338*a* before the vacuum is drawn through the trailing vacuum chamber 338*b* for receiving the continuous web 10. Additionally, the vacuum may be drawn for a longer period on the trailing vacuum chamber 338*b* after the vacuum has been removed from the leading vacuum chamber 338*a* when placing the cut pad 11 on the receiving surface 25.

FIG. 21 provides a first embodiment 800 of a preferred puck 301 according to the present invention. The puck 800 has a puck body 802 having a first web surface 804, a support surface 806 preferably oppositely disposed from the web surface 804, and a bearing shaft 808 depending from the support surface 806. The bearing shaft 808 is adapted to be rotatably supported by the puck support 303, such as being rotatably held in the bearing aperture 710 in the puck support head 700. The puck body 802 includes a vacuum chamber (not shown) within the body 802. Communicating fluidly with the vacuum chamber are preferably a plurality of web vacuum holes 810 extending through the web surface 804 and a plurality of support vacuum holes (not shown) extending through the support surface 806. The web vacuum holes 810 are provided about the web surface 804, and may be evenly spaced and provided near the perimeter of the web surface 804. The support vacuum holes provide a means for drawing a vacuum through the web vacuum holes 810 and the vacuum chamber in the puck body 802. Preferably, the support vacuum holes are mateable and adapted to cooperate with the vacuum apertures 704 extending into the puck support 303. By imparting a force to the bearing shaft 808, the puck 301 may be spun from a web-receiving orientation 801 to a web-placement orientation 803. Such force may be applied to the bearing shaft 808 by way of the spin linkage 327 that is coupled to the spin cam follower 325, which is disposed at least partially in the spin cam race 321. Though any web-placement orientation 803 angle may be desirable, the depicted angle 805 is ninety degrees from the web-receiving orientation 801.

FIG. 22A, FIG. 22B and FIG. 23 provide a second embodiment 850 of a preferred puck 301 according to the present invention. The puck 850 has a puck body 852 having a first web surface 854, a support surface 856 preferably oppositely disposed from the web surface 854, and a bearing shaft 858 depending from the support surface 856. The bearing shaft 858 is adapted to be rotatably supported by the puck support 303, such as being rotatably held in the bearing aperture 710 in the puck support head 700. The puck body 852 includes a vacuum chamber (not shown) within the body 852. Communicating fluidly with the vacuum chamber are preferably a plurality of web vacuum holes 860 extending through the web surface 854 and a plurality of support vacuum holes 862 extending through the support surface 856. The web vacuum holes 860 are provided about the first web surface 854, and may be evenly spaced and provided near at least a portion of the perimeter of the web surface 852. The support vacuum holes 862 provide a means for drawing a vacuum through the web vacuum holes 860 and the vacuum chamber in the puck body 852. Preferably, the support vacuum holes 862 are mateable and adapted to cooperate with the vacuum apertures 704 extending into the puck support 303. By imparting a force to the bearing shaft 858 or other portion of the puck 301, the puck 301 may be spun from a web-receiving orientation 851 to a web-placement orientation 853. Such force may be applied to the bearing shaft 858 by way of the spin linkage 327 that is coupled to the spin cam follower 325, which is disposed at least partially in the spin cam race 321. Though any web placement position 853 angle may be desirable, the depicted angle 855 is ninety degrees from the web receiving position 801.

In addition to the first web surface 854, this embodiment 850 preferably includes a pair of end web surfaces 864, which may be slidably disposed upon a pair of rails 866. To effect the slide of the end web surface 864, in a generally up-and-out manner, a dish cam 868 may be provided between a desired puck support 303 and the puck 301. The dish cam 868 preferably includes at least one cam groove 870 having a changing radius. Thus, when the puck 301 is in the web receiving position 851, the end web surfaces 864 are in a first position, preferably nearer the puck body 852. As the puck 301 spins to the web placement position 853, an end web cam follower 872 that is placed in the cam groove 870 causes the end web surface 864 to slide along the rails 866 to a second position, preferably further from the puck body 852. The end web surfaces 864 are also preferably provided with a plurality of web vacuum holes 860 in fluid communication with an end web vacuum chamber 874. The end web vacuum chamber 274 is preferably in fluid communication with the vacuum chamber (not shown) in the puck body 852. Such fluid communication between the end web vacuum chamber 274 and puck body 852 vacuum chamber may be provided by one or more vacuum bellows 876.

Figure 24:
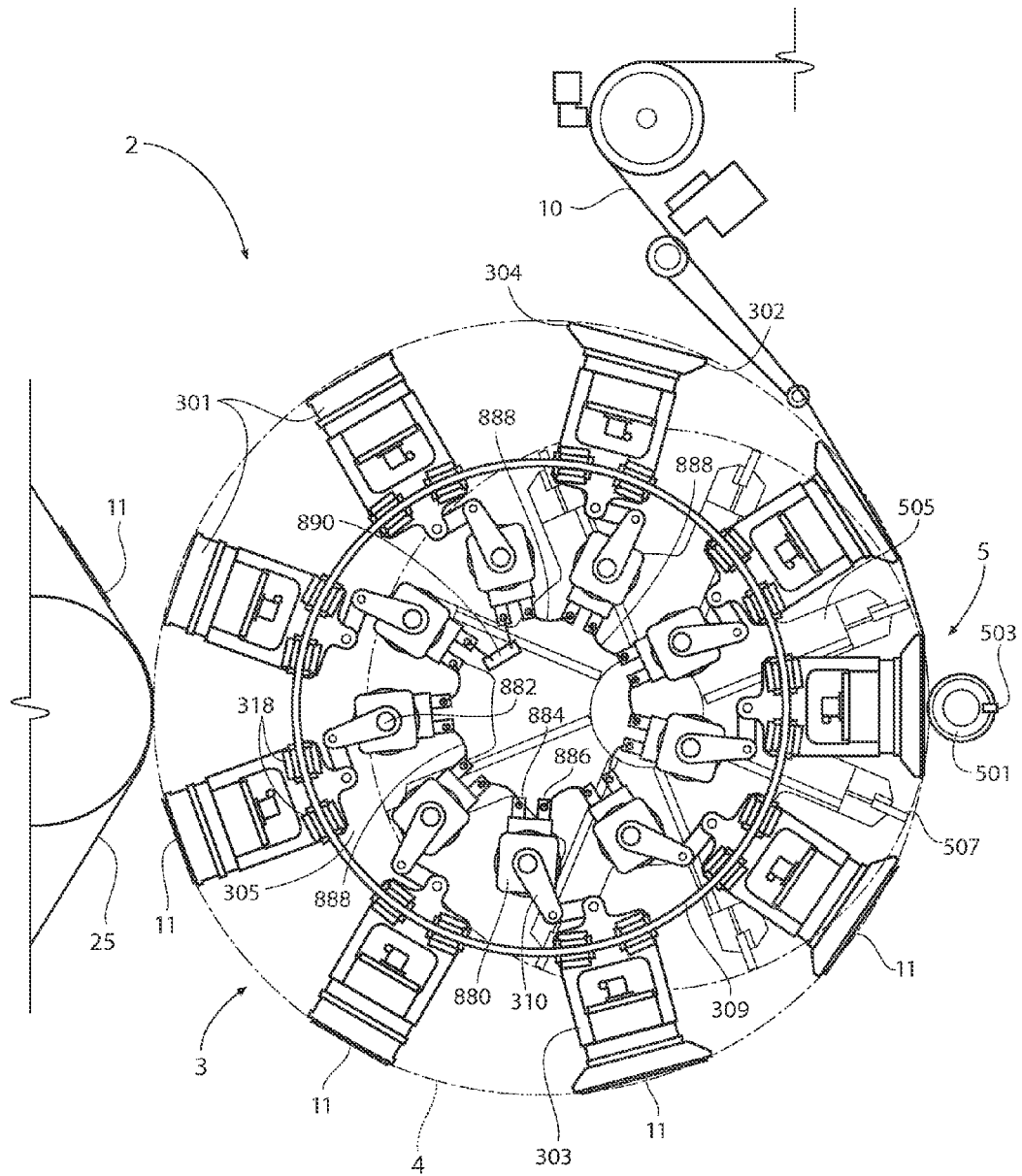
FIG. 24 is a front elevation view of a second embodiment of a system according to the present invention.
Figure 25:
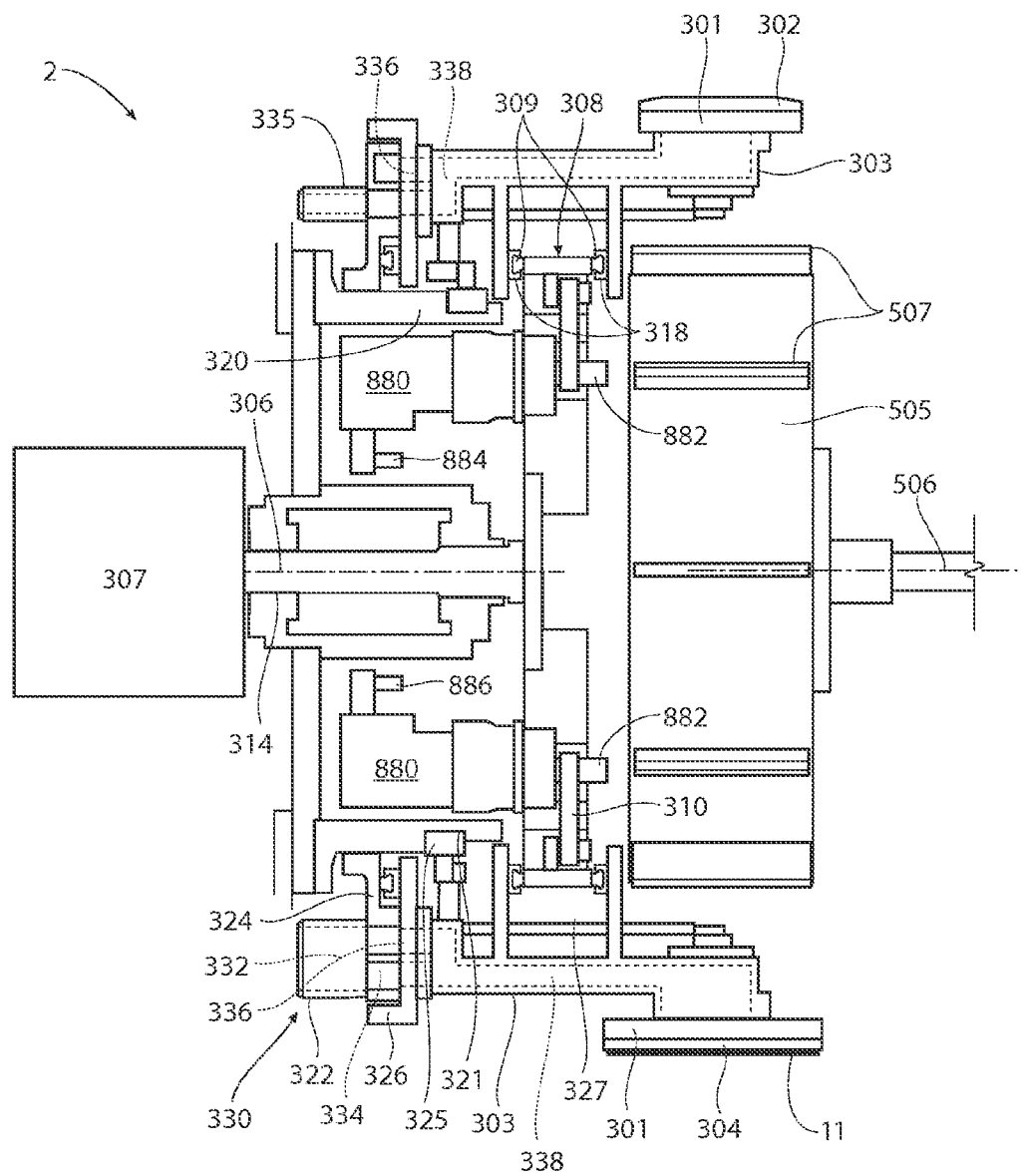
FIG. 25 is a right side elevation view of the embodiment in FIG. 24, eliminating components that would otherwise obstruct the desired view, namely multiple pucks and anvil roll.

FIG. 24 and FIG. 25 depict a second embodiment 2 of an apparatus according to the present invention. Generally, in this embodiment 2, the pitch cam arrangement of the first embodiment has been replaced by a plurality of servo drives 880, each of which may control the relative circumferential movement of a puck 301 relative to the main puck wheel 305, to which the servo drives 880 are preferably mounted. The servo drives 880 preferably have a rotatable shaft 882 that may be coupled to the primary pitch linkage 310 to enable such control. The servo drives 880 preferably have a first electrical terminal 884 and a second electrical terminal 886, wherein the first electrical terminal 884 of a first servo drive 880 is electrically coupled to the second electrical terminal 886 of a second servo drive 880 and the second electrical terminal 886 of the first servo drive 880 is electrically coupled to the first electrical terminal of a third servo drive 880. Thus, the electrical connections may be provided by a plurality of electrical wires 888 in a daisy chain format. The servo drives 880 are preferably controlled by and communicatively coupled to a servo drive controller (not shown). Such communicative coupling may be provided by a slip ring 890 and a plurality of electrical wires (not shown). An example of servo drives 880 and a servo drive controller may be found in the Rexroth IndraDrive® Mi Drive System provided by Bosch Rexroth Corporation of Hoffman Estates, Ill.

Figure 26:
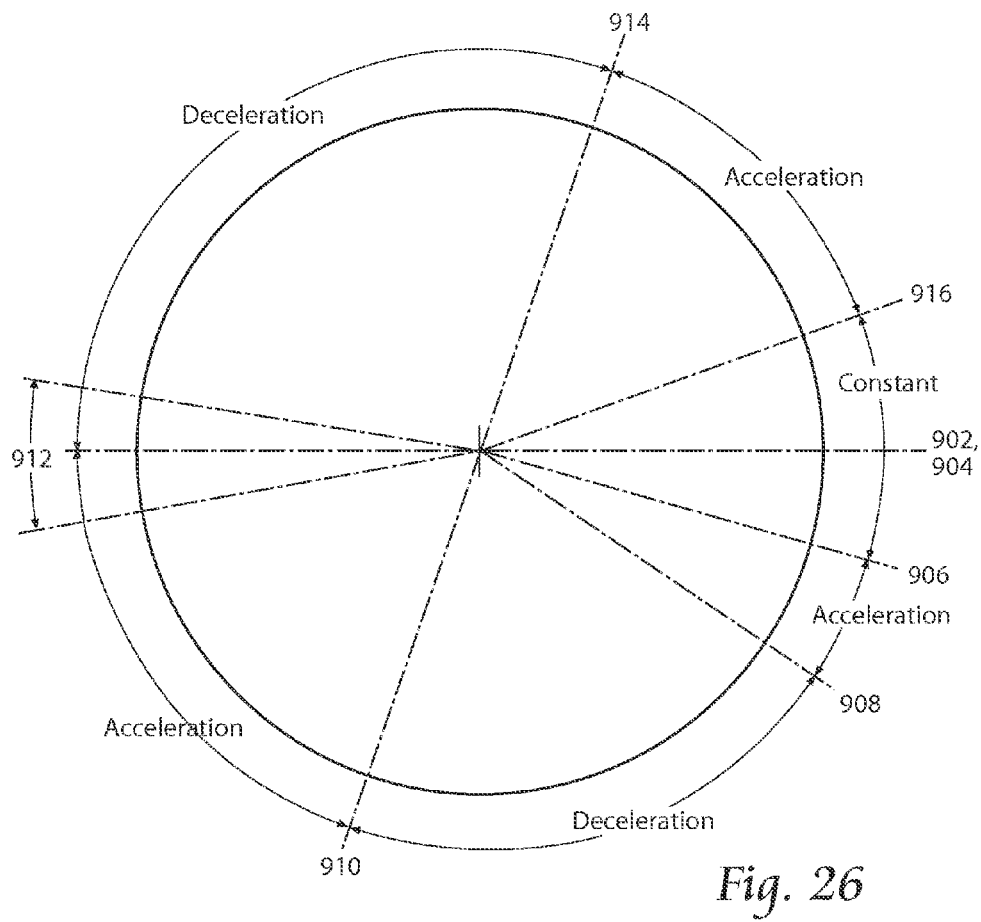
FIG. 26 is a front elevation schematic representation of a second preferred velocity profile of an apparatus according to the present invention.
Figure 27:
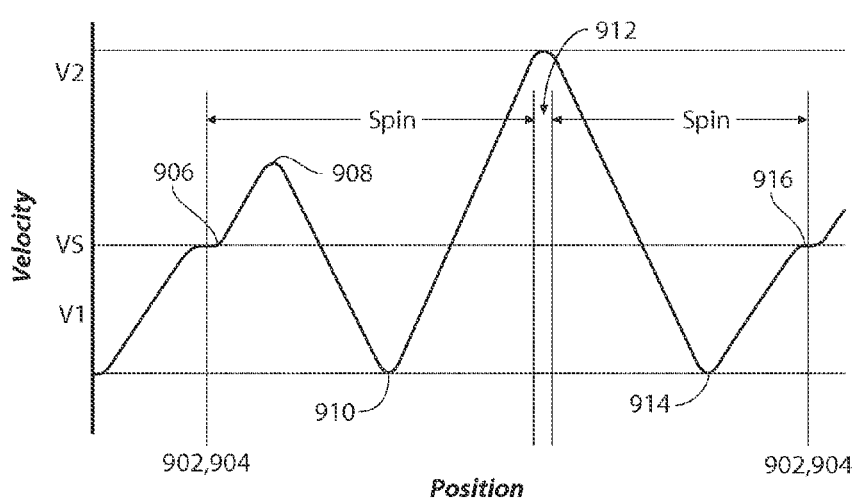
FIG. 27 is a graph view of the preferred velocity profile of FIG. 26.
Figure 28:
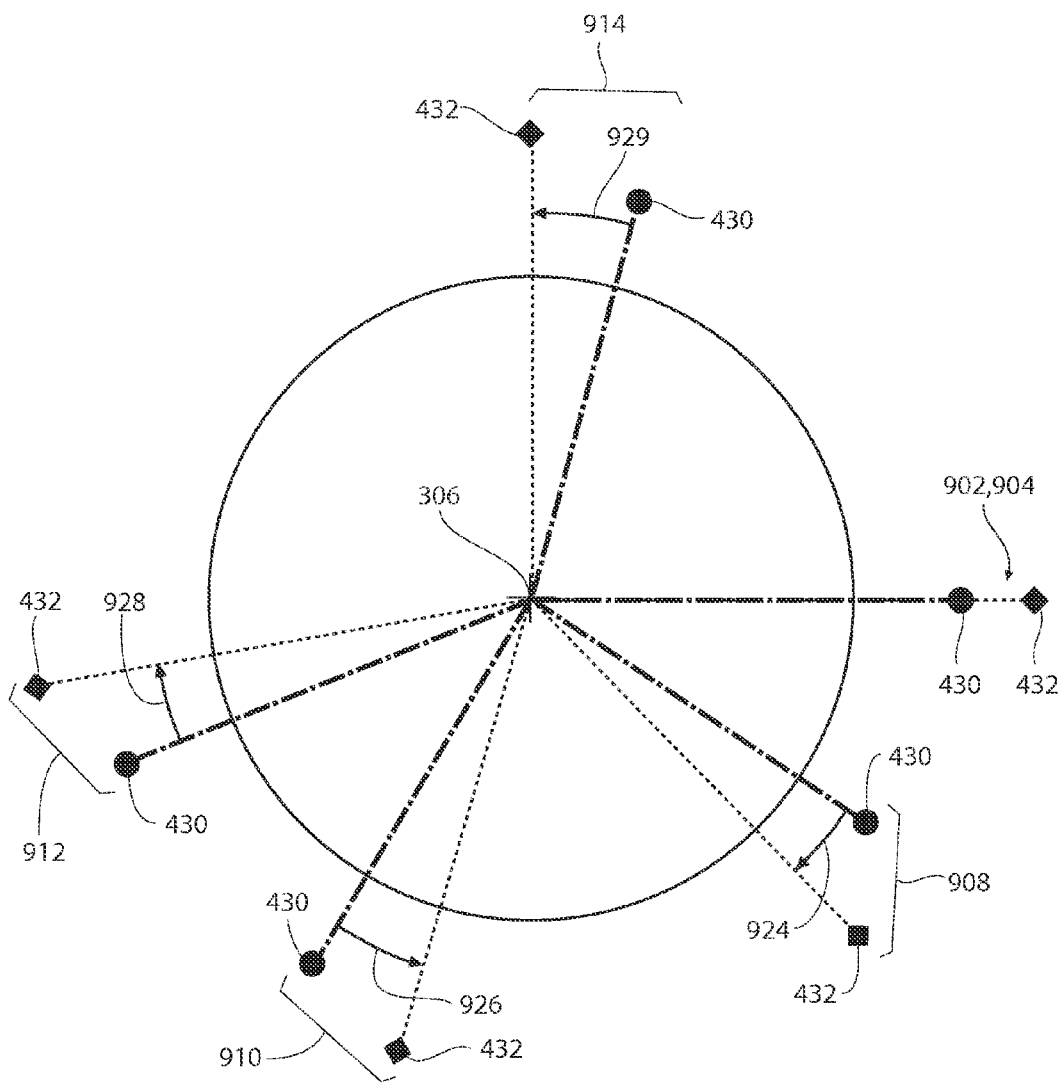
FIG. 28 is a front elevation schematic representation of puck position changing relative to a major axis of rotation, the puck following the velocity profile of FIG. 26.

FIG. 26, FIG. 27 and FIG. 28 provide a second preferred velocity profile and associated puck positioning of an apparatus according to the present invention. This profile may be referred to as an accel-to-place profile. With reference also to FIG. 1, the puck transfer mechanism 3 rotates about the puck transfer axis 306 at a relatively constant system velocity VS. When a puck 301 receives continuous web material 10, the puck 301 is moving at a first velocity, which may be the system velocity VS. A pad 11 is then cut from the continuous web 10. To create the pad 11, a first cut 902 is made proximate the leading puck edge 302 and a second cut 904 is made proximate the trailing puck edge 304. Just after a pad 11 is cut from the web material 10, the puck 301 may be accelerated 906 to prevent any collision with the subsequent neighboring puck 301 and may be decelerated 908 thereafter. Sometime after the trailing edge cut 904 and prior to placement 912 of the pad 11 on a receiving surface 25, the puck 301 spins to a desired angle and the velocity of the puck 301 may change 910 to achieve a desirable predetermined spacing. Upon or after reaching a velocity or relative spacing, the pad 11 is placed 912 on the receiving surface 25. After pad placement 912, the puck 301 may be decelerated and then accelerated 914 in preparation for the next rotation. The process then begins anew.

During periods of acceleration and deceleration, the pucks 301 change position relative to the major axis of rotation, the puck transfer axis 306. This can best be seen by reference to FIG. 28. A first reference point 430 represents a point on the shaft (314 on FIGS. 2 and 3) spinning about the puck transfer axis 306 at the relatively constant velocity VS during operation of the device 1. A second reference point 432 represents a position of a puck 301. While the shaft reference 430 may be rotating about the puck transfer axis 306 at a relatively constant velocity, the position of the puck reference 432 with respect to the shaft 314 may change a desirable amount, such as an increase of ten degrees or more of rotation during acceleration and a decrease of ten degrees or more of rotation during deceleration. To illustrate, the shaft reference 430 is generally radially aligned with the puck reference 432 during times of cutting 902,904. At the end 908 of the first acceleration, the puck reference 432 has changed position relative to the shaft reference 430 by a first distance 924. At the end 910 of the first deceleration period, the puck reference 432 has changed position relative to the shaft reference 430 by a second distance 926. Prior to pad placement 912, the puck 301 is again accelerated, and at the end of the second acceleration the puck reference 432 has advanced beyond the shaft reference 430 by a third distance 928. At the end 914 of the second deceleration period, the puck reference 432 has changed position relative to the shaft reference 430 by a fourth distance 929. The first distance 924, second distance 926, third distance 928 and fourth distance 929 may be the same or different. By the time it is ready for the same puck 301 to proceed through the process again, however, both references 430,432 are aligned and ready for another revolution.

Figure 29:
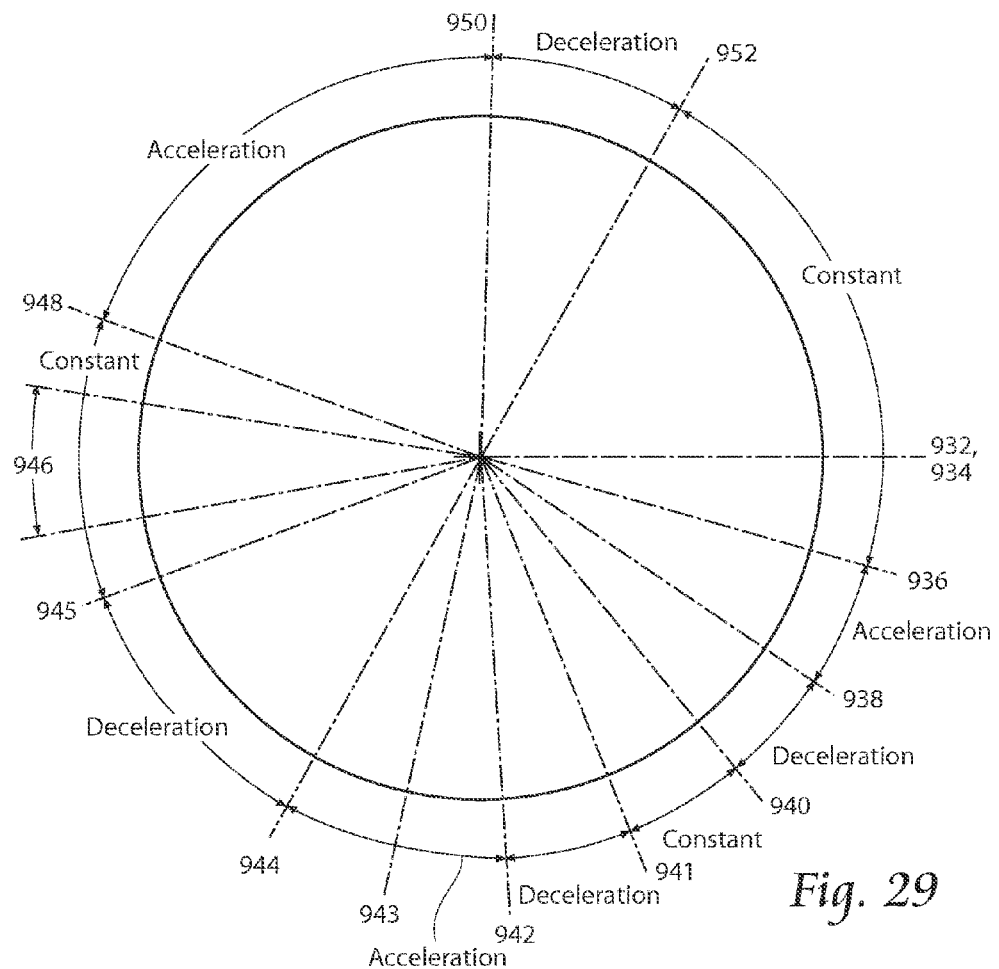
FIG. 29 is a front elevation schematic representation of a third preferred velocity profile of an apparatus according to the present invention.
Figure 30:
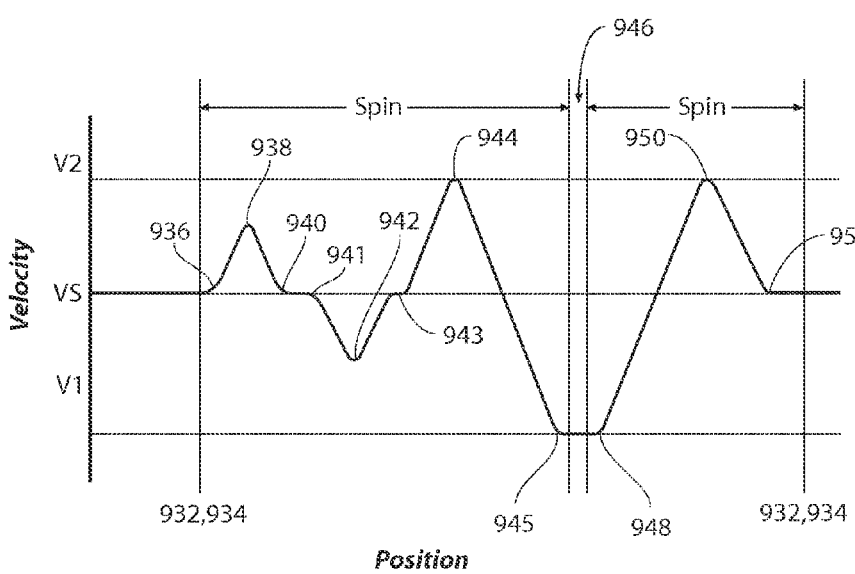
FIG. 30 is a graph view of the preferred velocity profile of FIG. 29.
Figure 31:
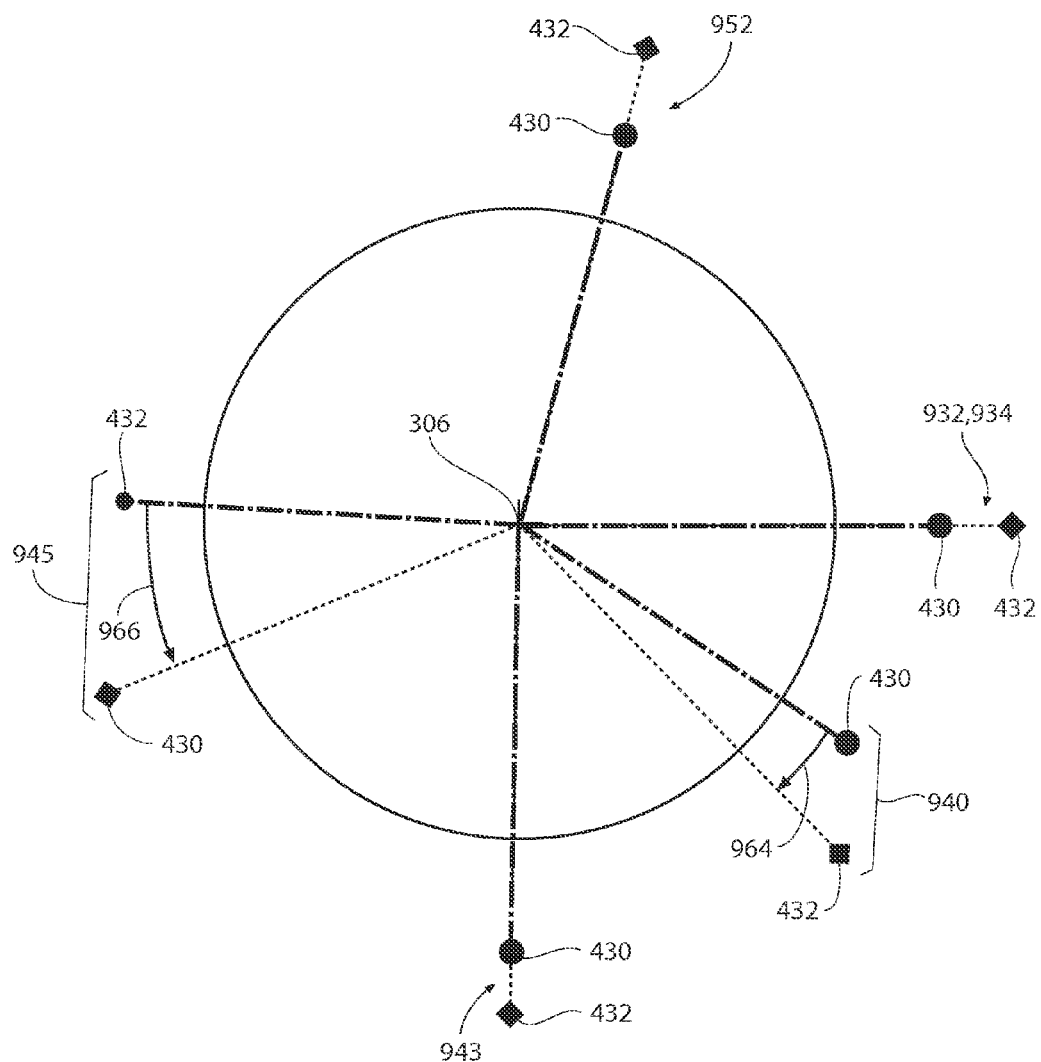
FIG. 31 is a front elevation schematic representation of puck position changing relative to a major axis of rotation, the puck following the velocity profile of FIG. 29.

FIG. 29, FIG. 30 and FIG. 31 provide a third preferred velocity profile and associated puck positioning of an apparatus according to the present invention. This profile may be referred to as a decel-to-place profile. With reference also to FIG. 1, the puck transfer mechanism 3 rotates about the puck transfer axis 306 at a relatively constant system velocity VS. When a puck 301 receives continuous web material 10, the puck 301 is moving at a first velocity, which may be the system velocity VS. A pad 11 is then cut from the continuous web 10. To create the pad 11, a first cut 932 is made proximate the leading puck edge 302 and a second cut 934 is made proximate the trailing puck edge 304. Just after a pad 11 is cut from the web material 10, the puck 301 may be accelerated 936 to prevent any collision with the subsequent neighboring puck 301 and may be decelerated 408 thereafter. Sometime after the trailing edge cut 934 and prior to placement 946 of the pad 11 on a receiving surface 25, the puck 301 spins to a desired angle and the velocity of the puck 301 may change 944 to achieve a desirable predetermined spacing. Upon or after reaching a velocity or relative spacing, the pad 11 is placed 946 on the receiving surface 25. After pad placement 946, the puck 301 may be accelerated 948 and then decelerated 950 in preparation for the next rotation. The process then begins anew.

During periods of acceleration and deceleration, the pucks 301 change position relative to the major axis of rotation, the puck transfer axis 306. This can best be seen by reference to FIG. 31. A first reference point 430 represents a point on the shaft (314 on FIGS. 2 and 3) spinning about the puck transfer axis 306 at the relatively constant velocity VS during operation of the device 1. A second reference point 432 represents a position of a puck 301. While the shaft reference 430 may be rotating about the puck transfer axis 306 at a relatively constant velocity, the position of the puck reference 432 with respect to the shaft 314 may change a desirable amount, such as an increase of ten degrees or more of rotation during acceleration and a decrease of ten degrees or more of rotation during deceleration. To illustrate, the shaft reference 430 is generally radially aligned with the puck reference 432 during times of cutting 932,934. At the end 940 of a first acceleration, the puck reference 432 has changed position relative to the shaft reference 430 by a first distance 964. At the end 410 of the first deceleration period, the puck reference 432 has changed position relative to the shaft reference 430 by a second distance 436. Prior to pad placement 946, the puck 301 may be decelerated, and at the end of the second acceleration the puck reference 432 has advanced beyond the shaft reference 430 by a third distance 438. At the end 414 of the second deceleration period, the puck reference 432 has changed position relative to the shaft reference 430 by a fourth distance 436. The first distance 434, second distance 436, third distance 438 and fourth distance 439 may be the same or different. By the time it is ready for the same puck 301 to proceed through the process again, both references 430,432 are aligned and ready for another revolution.

Figure 32:
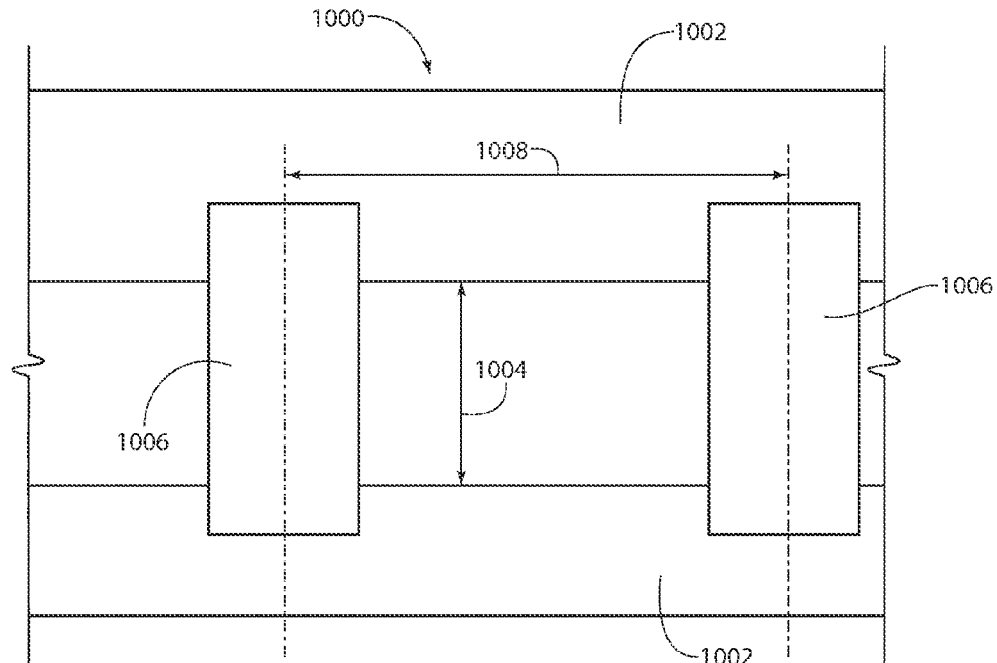
FIG. 32 is a top plan view of a prior ladder web construction.
Figure 33:
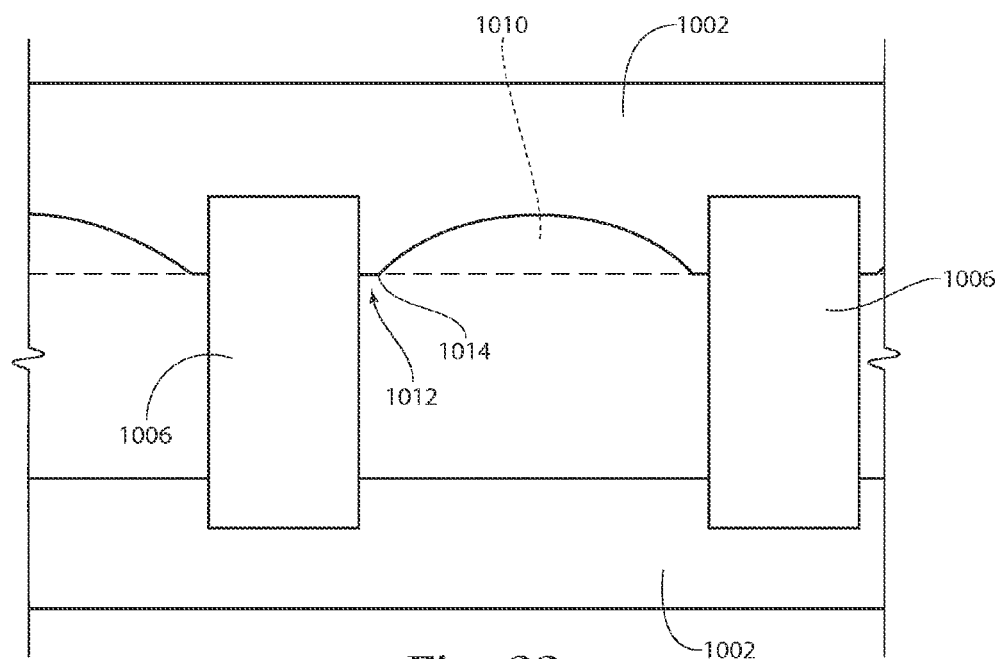
FIG. 33 is a top plan view of the web construction of FIG. 32 after having been trimmed.

A system according to the present invention may, in addition to a transfer mechanism, include an improved trimming assembly. In the past, it was common to construct a ladder web assembly, such as that 1000 shown in FIG. 32. The ladder web assembly 1000 generally includes a plurality of stringer or stile webs 1002 running at least substantially parallel to each other and spaced by a gap 1004 of a preferred distance. The stringer webs 1002 may consist of a single web layer or may comprise a compound web assembly. Indeed, the stringer webs 1002 may include elastic members deposited in a desired pattern. Spanning the gap 1004, there is placed a plurality of rung or step web assemblies 1006. The rung web assemblies 1006 are preferably discrete assemblies placed at a desire spacing or pitch 1008. The rung web assemblies 1006 may consist of a single web layer or may comprise a compound web assembly, such as an insert 11 provided by a transfer mechanism 3. Indeed, the rung web assemblies 1006 may include elastic components deposited in a desired pattern so as to at least partially span the gap 1004. In prior systems, it was common to trim one of the stringer web assemblies 1002 to provide a final product having a purportedly improved fit. For instance, as shown in FIG. 33, cutout portions 1010 may have been removed from one of the stringer web assemblies 1002. Such removal assisted in providing a wearable product, such as a diaper, thought to have an improved fit. One problem noticed with such prior trimming was that the interface between, or juncture of, 1012 the stringer web assemblies 1002 and the rung web assemblies 1006 was noticeably discontinuous, as can be seen by the remaining pointed, or otherwise convex, portion 1014 of the stringer web assembly 1000 after trimming. While such transition or interface 1012 between the stringer web assembly 1002 and the rung web assembly 1006 may appear to be a seemingly innocuous construct, sometimes significant discomfort was experienced by users of products manufactured in such manner. Additionally, in the past, upon formation of a ladder web assembly 1000, such assembly 1000 was conveyed some distance prior to the trimming operation. Thus, the formation of the assembly 1000 occurred at a first location using, for example, a first compression backing roller, and then the assembly 1000 was conveyed some distance to a cutting unit for trimming as described.

Figure 34:
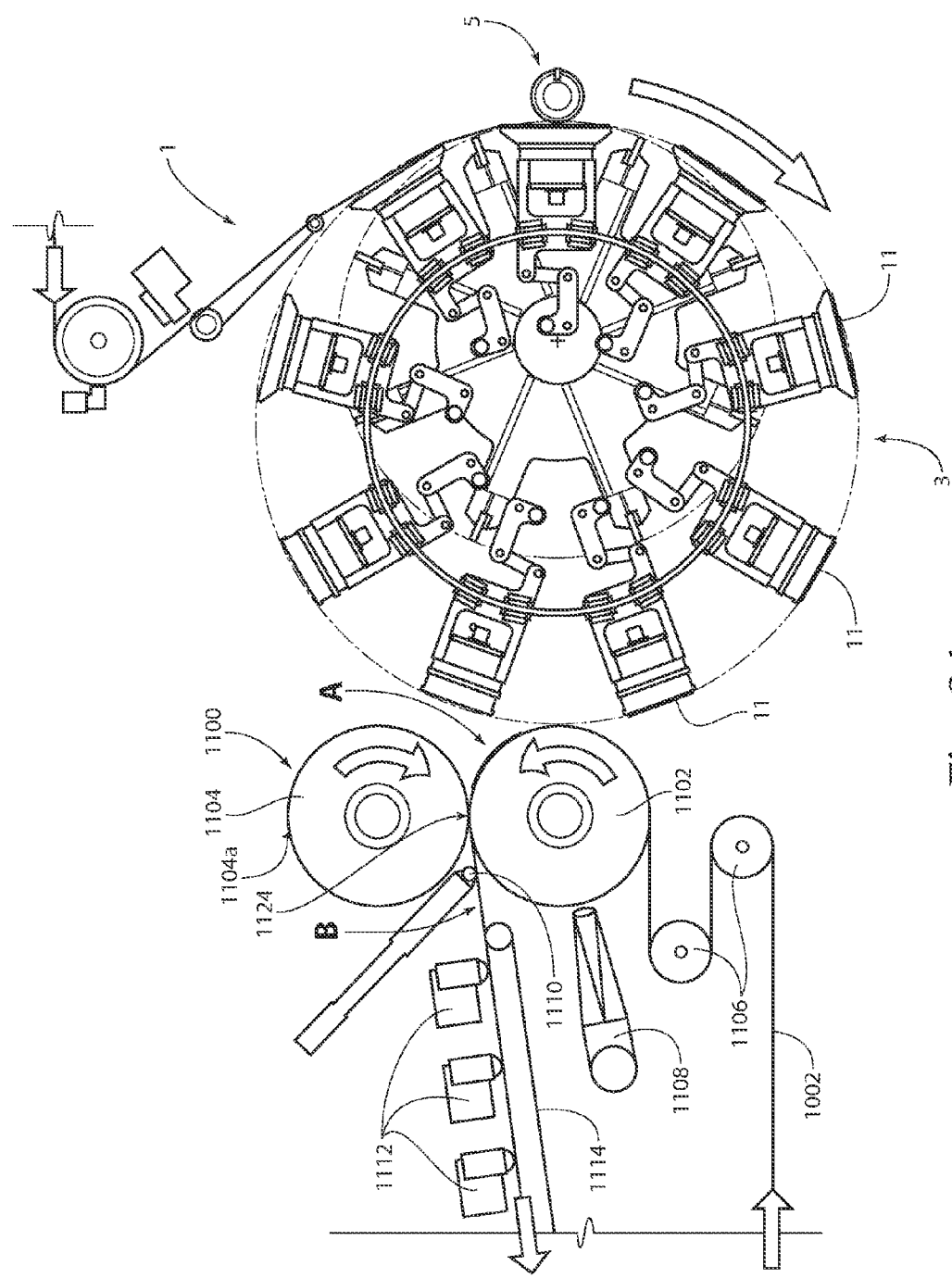
FIG. 34 is a side elevation view of an alternate embodiment of a system according to the present invention.

Embodiments according to the present invention include systems and methods adapted to improving the interface between stringer web assemblies and rung web assemblies in a ladder web construction. An embodiment of a system according to the present invention is shown in FIG. 34. The system preferably includes an improved ladder web cutting assembly 1100. The cutting assembly 1100 generally includes means for trimming a ladder web to provide an at least substantially continuous cut at the interface of ladder web stringers and rungs. One mechanism that may be used to carry out such trimming operation is a cutting assembly including an anvil roller 1102 and a die roller 1104. Die roller 1104 may include a die, knife or similar cutting mechanism 1104a attached to the roller 1104. While the arrangement of the die roller 1104 elevated above the anvil roller 1102, as shown, is preferred, other arrangements are deemed within the scope of the invention. In any event, the ladder web assembly 1000 is preferably formed on the anvil roller 1102. The stringer web assemblies 1002 are supplied to the process, shown entering at the lower left of FIG. 34. One or more directional feed rollers 1106 may be provided to ensure proper transfer of the stringer webs 1002 to the anvil roller 1102. The stringer webs 1002 are received onto the anvil roller 1102 and thereafter a rung web assembly 1006 is supplied, in the form of an insert 11, and adhered to the stringer webs 1002 to span the ladder web gap 1004. The compression used to mate the rung web 1006 to the stringer webs 1002 is thus at least partially supplied by the anvil roller 1102 in cooperation with the apparatus supplying the rung web 1006, in this case the transfer mechanism 3. The ladder web 1000 is then rotated to a nip 1124 created between the anvil roller 1102 and the die roller 1104 for trimming. The cooperation of the die roller 1104 and the anvil roller 1102 trims the ladder web assembly 1000 in a preferably continuous fashion, at least at the juncture of the stringer webs 1002 and the rung webs 1006, thus trimming both at least one stringer web 1002 and a rung web 1006. As will be discussed further, the trimming step results in a trimmed ladder web 1200 and scrap portions 1210. The scrap portions 1210 preferably remain on the anvil roller 1102 after the respective trimmed ladder web 1000 is removed therefrom, and collected by a waste vacuum assembly 1108. After such trimming step, further adhesive compression may be supplied to the trimmed ladder web by a first compression roller 1110, and the trimmed ladder web is conveyed for further processing, such as further compression by a plurality of compression rollers 1112 in cooperation with a conveyor belt 1114. Further processing may also include product cutting at the insert pitch, though 180 degrees out of phase with the inserts, product folding and product packaging.

Figure 35A:
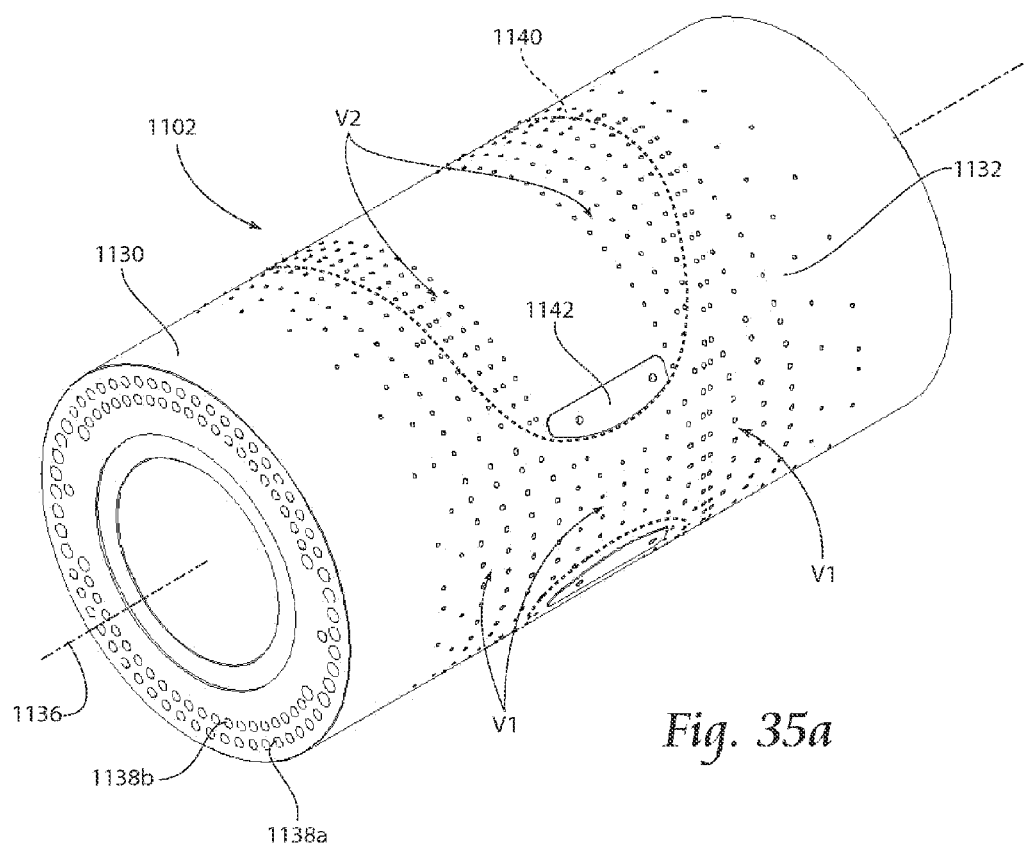
FIG. 35a is a perspective view of an embodiment of an anvil roller that may be used in the system embodiment of FIG. 34.
Figure 35B:
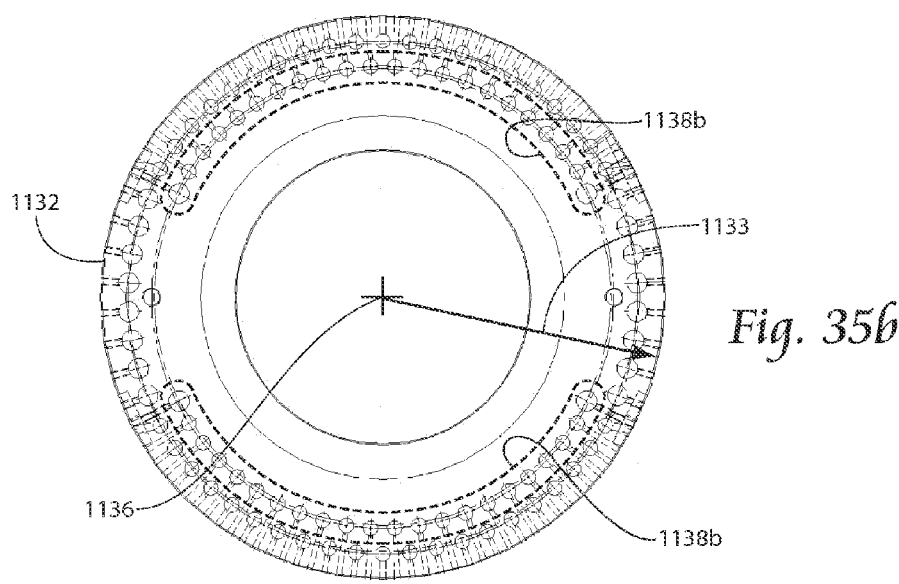
Figure 35C:
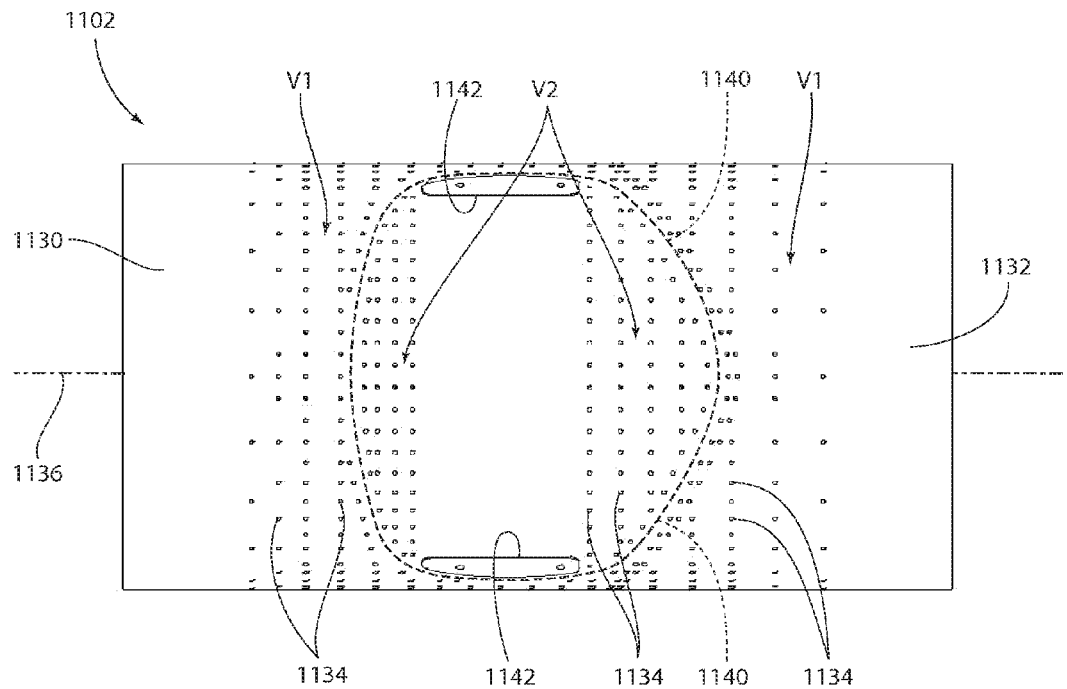

Turning now to FIGS. 35a-c, a preferred anvil roller 1102 may be seen. The anvil roller 1102 is generally preferably in the shape of an at least substantially cylindrical drum 1130 having an outer surface 1132 disposed at a predetermined radius 1133 from an axis of rotation 1136. A preferred radius 1133 may be calculated by the following formula:

$$\text{Radius}_{anvil} \approx (\tfrac{1}{2})((N*PP)/\pi),$$

where N is an integer, such as two, and PP is the product or insert pitch 1008. The radius 1133 may be calculated to account for a desired percent-stretch of the product, such as a 1-10 percent stretch, and preferably a 2% stretch. Where a percent stretch is desired, a drum radius formula may include the following:

$$\text{Radius}_{anvil} \approx (\tfrac{1}{2})((N*PP*S)/\pi),$$

where S is the number 1 plus the decimal representation of the desired percent-stretch. In other words, if a 2% stretch is desired, S would equal 1.02.

Extending through the outer surface 1132 of the anvil roller 1102 are a plurality of vacuum apertures 1134. The vacuum apertures 1134 are preferably divided into a plurality of vacuum zones, such as zones V1 and V2. The apertures 1134 of the vacuum zones V1,V2 are preferably respectively associated with one or more vacuum ports 1138, which may be provided through an end of the anvil roller 1102. For instance, the apertures 1134 of vacuum zone V1 may be associated with a first set 1138a of vacuum ports 1138 and the apertures 1134 of vacuum zone V2 may be associated with a second set 1138b of vacuum ports 1138. In this manner, vacuum application timing and pressure drawn through the apertures 1134 may be controlled separately between the plurality of zones V1,V2. For instance, the plurality of zones V1,V2 may be arranged so that one zone V1 is associated with a trimmed ladder web and the other zone V2 is associated with the scrap trimmings removed therefrom. Thus, the vacuum zones V1,V2 may be situated on opposite sides of a preferred cutting path 1140. A preferred cutting path 1140 may at least partially follow substantially adjacent to elastic members that are included in either the stringer web assemblies or the rung web assemblies or both. In or proximate the cutting path 1140, there may be an anvil insert 1142. The anvil insert 1142 may be replaceable component of the anvil roller 1102, such by being fastened thereto with threaded fasteners. The anvil insert 1142 may include vacuum apertures 1134, preferably associated with one or more of the vacuum zones V1,V2. Most preferably, such apertures 1134 on the anvil insert 1142 are associated with the same vacuum zone V1,V2 that is located on the same side of the cutting path 1140 as a majority of the anvil insert 1142, V2 in the depicted embodiment. In any event, it is preferred that the cutting operation is performed while vacuum is being drawn through all vacuum zones at least laterally at the point of the nip 1124. That is, where the die roller 1104, which has a cutting implement 1104a formed in a desired shape to cooperate with the anvil roller 1102, and the anvil roller 1102 meet, it is preferred that all vacuum zones V1,V2 disposed laterally along the anvil roller axis 1136 are activated. Thus, the ladder web can be said to be preferably cut while vacuum is being drawn therethrough.

Figure 36:
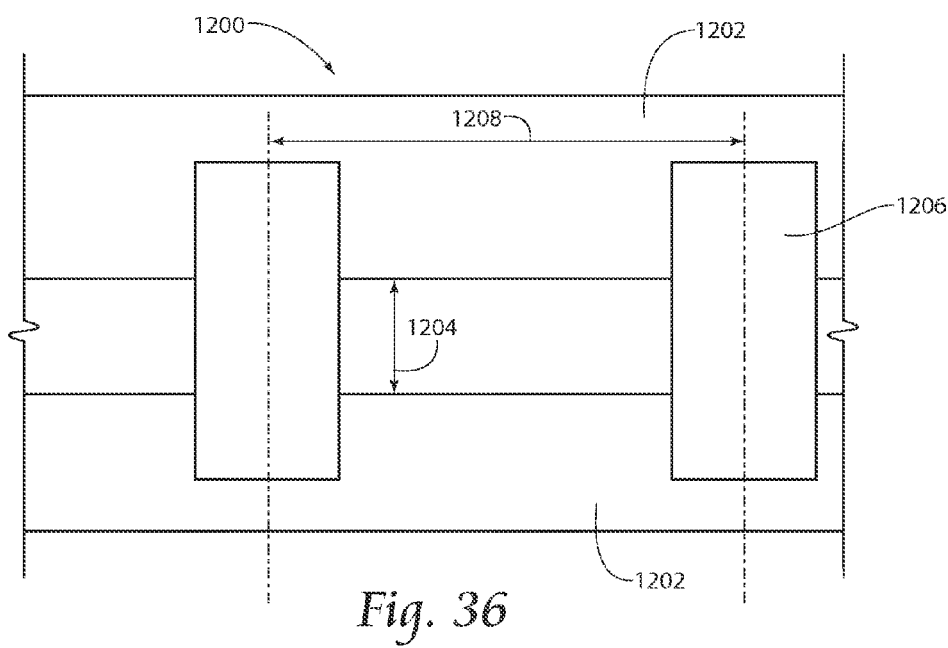
FIG. 36 is a top plan view of an alternate embodiment of a ladder web construction.

Referring now to FIGS. 34-37, a preferred process according to the present invention will be explained. In FIG. 36, an assembled ladder web 1200 is shown. Similar in construction to the ladder web 1000 previously discussed, like numerals refer to similar or identical structure to the prior web 1000. This alternative ladder web 1200 may include a reduced gap 1204, thus allowing more overlap between one or both of the stringer web assemblies 1202 and the rung web assemblies 1206. The web 1200 shown is the web that could be viewed at point A in FIG. 34. That is, the stringer web assemblies 1202 have been supplied to the anvil roller 1102, and a vacuum drawn therethrough. Preferably after the stringer web assemblies 1202 are received by the anvil roller 1102, a rung web assembly 1206 is supplied and adhered to the stringer web assemblies 1202, and a vacuum drawn therethrough. While the ladder web assembly 1200 is being drawn to the anvil roller 1102 with vacuum pressure drawn through the vacuum apertures 1134, the die roller 1104 cooperates with the anvil roller 1102 to cut a desired shape from the ladder web assembly 1200. The desired cutting path 1140 preferably includes a substantially continuous cut between at least one of the stringer web assemblies 1202 and one of the rung web assemblies 1206. Preferably substantially immediately after the nip 1124, vacuum pressure is removed from the product vacuum zone V1, and the trimmed ladder web 1200 is allowed to proceed to further processing. However, vacuum pressure is preferably maintained in the scrap vacuum zone V2 longer than the product vacuum zone V1 so that the trimmed portions 1210 may be carried to a waste vacuum 1108 for disposal. Vacuum pressure is preferably removed from the scrap vacuum zone V2 when the trimmed portions 1210 are proximate the waste vacuum 1108 for collection. Generally speaking, in the depicted arrangement, vacuum pressure may be applied to both zones V1 & V2 at about the six o'clock position of the anvil roller 1102. Vacuum pressure is preferably removed from the product vacuum zone V1 at about the eleven o'clock position and vacuum pressure is preferably removed from the scrap vacuum zone V2 at about the nine o'clock position.

Figure 37:
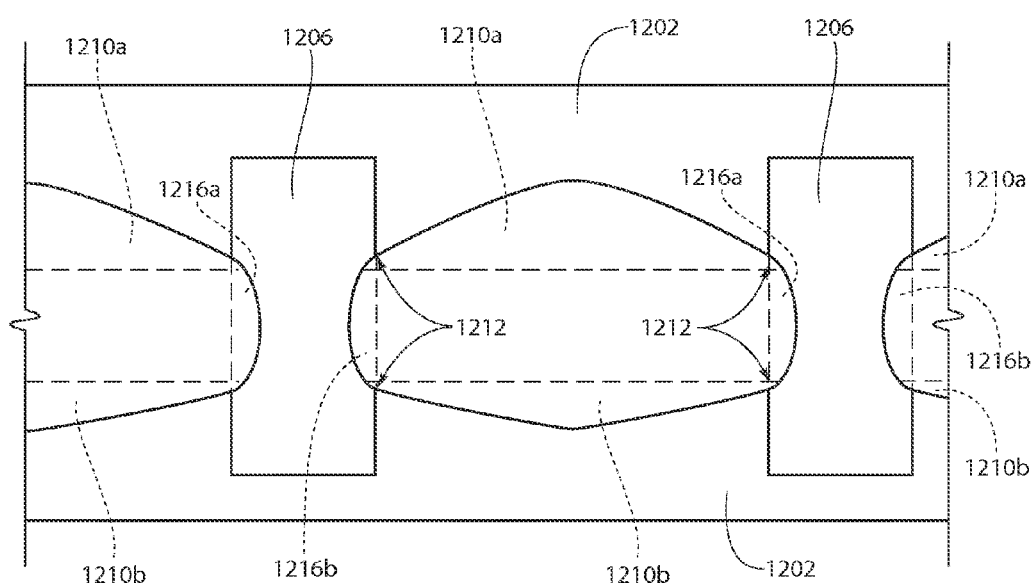
FIG. 37 is a top plan view of the web construction of FIG. 32 after having been trimmed according to the present invention.

Turning now to FIG. 37, a trimmed ladder web assembly 1200 according to the present invention may be seen. The intersections 1212 of the stringer webs 1202 with the rung webs 1206 have been rendered substantially continuous for added comfort of a worn product, for example. Two scrap portions 1210a,1210b have been trimmed from the stringer webs 1202, and two scrap portions 1216a,1216b have been trimmed from preferably each of the rung webs 1206.

The foregoing is considered as illustrative only of the principles of the invention. Furthermore, since numerous modifications and changes will readily occur to those skilled in the art, it is not desired to limit the invention to the exact construction and operation shown and described, the details may be changed without departing from the invention.

What is claimed is:

1. A web cutting system for use with a single transfer insert placement mechanism having at least one puck for transferring a discrete web and a continuous web feeding mechanism for feeding a continuous web, said web cutting system comprising:
    first and second rollers having substantially parallel axes and aligned with one another to form a nip at their juncture;
    said system being arranged for circumferentially modifying the position and spacing of said puck;
    an anvil attached to one of said first and second rollers;
    a die attached to the other of said first and second rollers;
    said anvil having a ladder assembly with at least one directional feed roller rotatably feeding said continuous web into said nip;
    at least one vacuum source coupled to one of said first and second rollers and a plurality of vacuum apertures formed in said same roller; and
    one of said first and second rollers positioned adjacent to said single transfer insert placement mechanism and to said continuous web feeding mechanism whereby said continuous web is applied to said roller having the vacuum source coupled thereto and at least one discrete web is transferred from said puck to said roller having the vacuum source coupled thereto.

2. The web cutting system of claim 1 further comprising at least one compression roller, said compression roller positioned downstream of said nip.

3. The web cutting system of claim 1 further comprising a waste vacuum, said waste vacuum positioned adjacent said roller having the vacuum source coupled thereto.

4. The web cutting system of claim 1 wherein said roller having the vacuum source coupled thereto further includes the anvil attached thereto.

5. The web cutting system of claim 1 wherein said apertures on said roller having the vacuum source coupled thereto are segregated into first and second vacuum zones.

6. The web cutting system of claim 1 wherein said apertures on said roller having the vacuum source coupled thereto are segregated into a plurality of vacuum zones.

7. The web cutting system of claim 5 wherein the vacuum source coupled to said first vacuum zone is different from the vacuum source coupled to said second vacuum zone.

8. The web cutting system of claim 1 further comprising a plurality of dies attached to one of said first and second rollers.

9. The web cutting system of claim 1 further comprising a plurality of anvils attached to one of said first and second rollers.

10. The web cutting system of claim 1 wherein the die comprises at least one knife.

* * * * *